(12) United States Patent
Loh et al.

US011401520B2

(10) Patent No.: US 11,401,520 B2
(45) Date of Patent: Aug. 2, 2022

(54) COMPOSITIONS AND METHODS COMPRISING PERMUTED PROTEIN TAGS FOR FACILITATING OVEREXPRESSION, SOLUBILITY, AND PURIFICATION OF TARGET PROTEINS

(71) Applicant: The Research Foundation for the State University of New York, Syracuse, NY (US)

(72) Inventors: Stewart N. Loh, Manlius, NY (US); Jeung-Hoi Ha, Manlius, NY (US)

(73) Assignee: THE RESEARCH FOUNDATION FOR THE STATE UNIVERSITY OF NEW YORK, Albany, NY (US)

(*) Notice: Subject to any disclaimer, the term of this patent is extended or adjusted under 35 U.S.C. 154(b) by 164 days.

(21) Appl. No.: 16/342,459

(22) PCT Filed: Oct. 23, 2017

(86) PCT No.: PCT/US2017/057881
§ 371 (c)(1),
(2) Date: Apr. 16, 2019

(87) PCT Pub. No.: WO2018/076008
PCT Pub. Date: Apr. 26, 2018

(65) Prior Publication Data
US 2019/0270998 A1    Sep. 5, 2019

Related U.S. Application Data

(60) Provisional application No. 62/411,295, filed on Oct. 21, 2016, provisional application No. 62/518,207, filed on Jun. 12, 2017.

(51) Int. Cl.
| | | |
|---|---|---|
| *C12N 15/62* | (2006.01) |
| *C12P 21/02* | (2006.01) |
| *C07K 14/52* | (2006.01) |
| *C07K 14/195* | (2006.01) |
| *C07K 14/47* | (2006.01) |
| *C12N 9/10* | (2006.01) |

(52) U.S. Cl.
CPC ............ *C12N 15/62* (2013.01); *C07K 14/195* (2013.01); *C07K 14/4746* (2013.01); *C07K 14/52* (2013.01); *C07K 14/521* (2013.01); *C12N 9/104* (2013.01); *C12P 21/02* (2013.01); *C07K 2319/20* (2013.01); *C07K 2319/21* (2013.01); *C07K 2319/24* (2013.01); *C07K 2319/50* (2013.01)

(58) Field of Classification Search
None
See application file for complete search history.

(56) References Cited

U.S. PATENT DOCUMENTS

| | | |
|---|---|---|
| 6,303,128 B1 | 10/2001 | Webb et al. |
| 6,410,220 B1 | 6/2002 | Hodgson et al. |
| 2005/0130269 A1 | 6/2005 | Gokce et al. |
| 2014/0302078 A1 | 10/2014 | Masignani et al. |

FOREIGN PATENT DOCUMENTS

WO    2017/066441 A1    4/2017

*Primary Examiner* — Suzanne M Noakes
(74) *Attorney, Agent, or Firm* — Michael Krenicky; Lance Reich; Steven A. Wood, Jr.

(57) ABSTRACT

Provided are compositions and methods for used in solubilizing, stabilizing and expressing proteins. The proteins are fusion proteins that contain a protein of interest. The fusion proteins contain segments of Ribose Binding Protein (RBP) or Maltose Binding Protein (MBP). The fusion proteins can have the RBP or MBP segments flanking the target protein, and the RBP or MBP segments can be in the fusion protein in the same orientation as they normally occur (except for being interrupted by the target protein) or the segments can be permuted. Novel segments of the RBP and MBP are provided and result in improved expression and/or solubility of the proteins. Some examples include one or a combination of two complete or partial Histidine tags. Some examples allow for the target protein to be separated from all or a part of the fusion protein such as by enzymatic or non-enzymatic cleavage.

28 Claims, 17 Drawing Sheets
Specification includes a Sequence Listing.

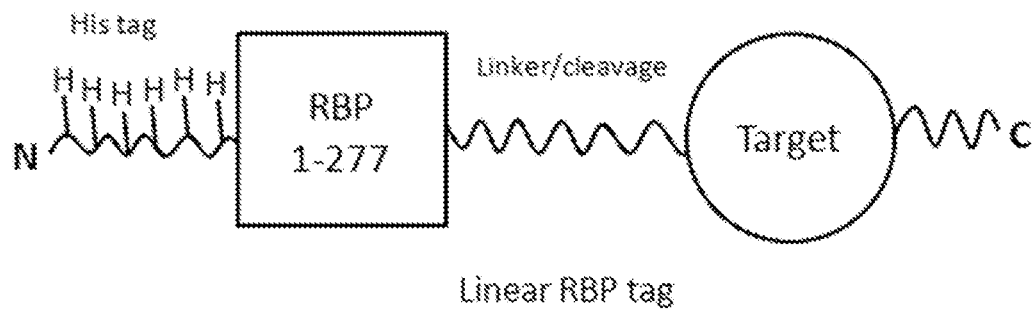
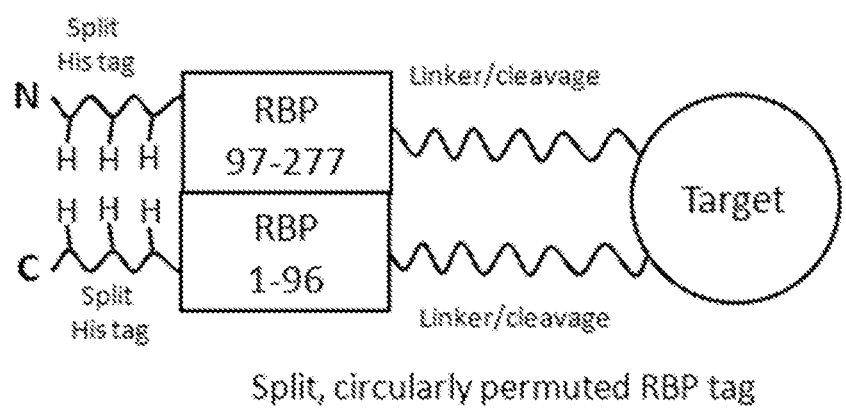
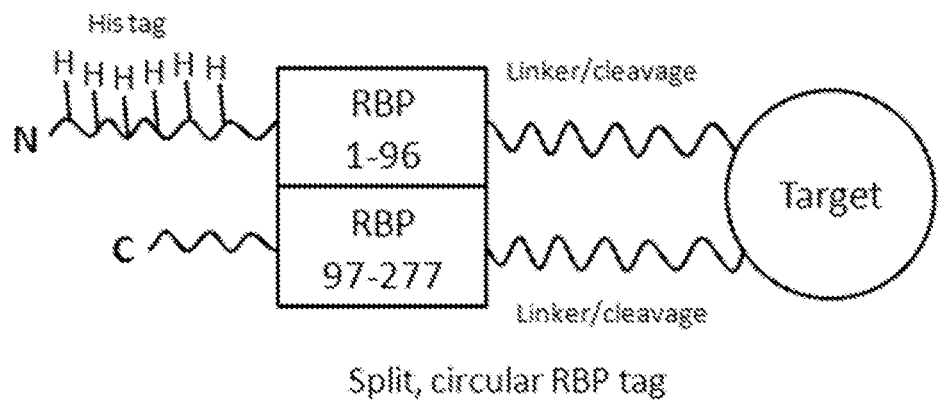
Figure 2

Split tteRBP s97 with multiple cloning site (MCS) for inserting target protein gene Legend:

Split-His tag 1 - [RBP97 - RBP277] - linker 1 - protease site 1 - MCS - protease site 2 - linker 2- [RBP1 - RBP96] - Split-His tag 2

AA Sequence:

| | |
|---|---|
| MGSSHHHHHHSSSGDVVSHIASDNVRGGEMAABFIAKALRGKGNVVELEG | 49 |
| IPGASAARDRGKGFDEAIAKYPDIKIVAKQAADFDRSKGLSVMENILQAQ | 99 |
| PKIDAVFAQNDEMALGAIKAIEAANRQGIIVVGFDGTEDALKAIKEGRMA | 149 |
| ATIAQQPALMGSLGVEMADKYLKGEKIPNFIPAELKLITKENVQGGSASG | 199 |
| GTSGGSSAAGLEVLFQGPAAAGGPSGTMGSGSGGLEVLFQGPGSSGGTAS | 249 |
| GGREGKTIGLVISTLRNPPFVTLKNGAEEKAKELGYKIIVEDSQNDSSKE | 299 |
| LSNVEDLIQQKVDVLLINPVDSDAVVTAIKEANSKNIPVITIDRSANGHH | 349 |
| HHH (SEQ ID NO:3) | |

DNA Sequence coding sequence:

```
   1 ATGGGTAGCT CACACCATCA CCATCACCAT TCGAGCTCGG GCGACGTAGT
  51 GTCGCATATC GCAAGCGATA ACGTCAAGGG AGGTGAGATG GCTGCCGAGT
 101 TCATTGCGAA AGCCTTAAAG GGCAAAGGGA ACGTCGTGGA ATTAGAGGGC
 151 ATCCCAGGAG CGTCGGCAGC TCGTGACCGC GGAAAAGGGT TTGACGAGGC
 201 TATTGCTAAG TACCCAGACA TCAAGATCGT GGCCAAACAA GCCGCCGACT
 251 TTGATCGCAG TAAGGGTTTG AGCGTTATGG AAAACATCTT ACAGGCCCAA
 301 CCGAAAATTG ATGCAGTGTT CGCGCAAAAT GATGAGATGG CTTTGGGTGC
 351 AATTAAAGCA ATTGAGGCTG CGAACCGCCA AGGTATTATC GTGGTCGGCT
 401 TCGACGGTAC AGAGGACGCG TTGAAGGCGA TTAAAGAAGG GAAGATGGCG
 451 GCGACCATTG CACAACAGCC GGCCTTGATG GGCTCGCTTG GGTCGAGAT
 501 GGCTGATAAA TATCTTAAGG GCGAAAAAAT CCCTAATTTT ATCCCCGCTG
 551 AATTGAAATT GATCACTAAA GAAAATGTGC AAGGGGGTTC TGCCTCTGGA
 601 GGGACAAGTG GTGGATCGAG TGCGGCCGGT TTGGAGGTTT TATTCCAGGG
 651 TCCAGCGGCC GCAGGTGGCC CGAGCGGGAC CATGGGCTCT GGATCCGGTG
 701 GCTTAGAAGT ATTATTCCAA GGTCCAGGTT CGTCAGGAGG GACGGCATCT
 751 GGAGGGAAAG AAGGCAAAAC CATCGGTCTG GTCATCAGTA CCTTGAATAA
 801 CCCCTTCTTT GTAACCTTGA AAAATGGCGC TGAGGAGAAA GCGAACGAAC
 851 TGGGATACAA GATCATCGTA GAGGATTCCC AGAATGACTC CTCGAAGGAG
 901 TTATCCAACG TTGAGGATTT AATTCAACAG AAGGTCGACG TACTGCTGAT
 951 TAACCCTGTA GATTCGGATG CTGTTGTAAC CGCCATTAAG GAAGCAAATA
1001 GCAAGAACAT TCCAGTTATT ACTATTGATC GCTCGGCCAA CGGGCACCAC
1051 CACCACCACT AA (SEQ ID NO:4)
```

Figure 9A

Split, circularly permuted RBP-MDM2 fusion

MDM2 amino acid sequence is in boldface. RBP, linkers, MCS, and protease sequences are identical to those above and in non-boldface.

AA sequence of the construct in Fig. 7:

```
MGSSHHHSSSGDVVSHIASDNVKGGEMAAEFIAKALKGKGNVVELEGIPG  49
ASAARDRGKGFDEAIAKYPDIKIVAKQAADFDRSKGLSVMENILQAQPKI  99
DAVFAQNDEMALGAIKAIEAANRQGIIVVGFDGTEDALKAIKEGKMAATI 149
AQQPALMGSLGVEMADKYLKGEKIPNFIPAELKLITKENVQGGSASGGTS 199
GGSSAAGLEVLFQGPAAAMCNTNMSVPTDGAVTTSQIPASEQETLVRPKP 249
LLLKLLKSVGAQKDTYTMKEVLFYLGQYIMTKRLYDEKQQHIVYCSNDLL 299
GDLFGVPSFSVKEHRKIYTMIYRNLVVVNQQESSDSGTSVSENRCHLEGG 349
SDQKDLVQELQEEKPSSSHLVSRPSTSSRRRAISETEENSDELSGERQRK 399
RHKSDSISLSFDESLALCVIREICCERSSSSESTGTPSNPDLDAGVSEHS 449
GDWLDQDSVSDQFSVEPEVESLDSEDYSLSEEGQELSDEDDEVYQVTVYQ 499
AGESDTDSFEEDPEISLADYWKCTSCNEMNPPLPSHCNRCWALRENWLPE 549
DKGKDKGEISEKAKLENSTQAEEGFDVPDCKKTIVNDSRESCVEENDDKI 599
TQASQSQESEDYSQPSTSSSIIYSSQEDVKEFEREETQDKEESVESSLPL 649
NAIEPCVICQGRPKNGCIVHGKTGHLMACFTCAKKLKKRNKPCPVCRQPI 699
QMIVLTYFPGSGGLEVLFQGPGSSGGTASGGKEGKTIGLVISTLNNPFFV 749
TLKNGAEEKAKELGYKIIVEDSQNDSSKELSNVEDLIQQKVDVLLINPVD 799
SDAVVTAIKEANSKNIPVITIDRSANGHHH (SEQ ID NO:5)
```

Figure 9A, continued

Split tteRBP s125 with multiple cloning site (MCS) for inserting target protein gene Legend:

Split-His tag 1 - [RBP125 - RBP277] - linker 1 - protease site 1 - MCS - protease site 2 - linker 2- [RBP1 - RBP124] - Split-His tag 2

AA Sequence:

MGSHHHKGNVVELEGIPGASAARDRGKGPDEAIAKYPDIKIVAKQAADPD 49

RSKGLSVMENILQAQPKIDAVFAQNDEMALGAIKAIEAANRQGIIVVGPD 99

GTEDALKAIKEGKMAATIAQQPALMGSLGVEMADKYLKGEKIPNFIPAEL 149

KLITKENVQGGSASGGTSGGSBAAGLEVLFQGPAAAGGPSGTPGSGSGGL 199

SVLFQGPGSSGGTASGGKEGKTIGLVISTLNNPFFVTLKNGAEEKAKELG 249

YKIIVEDSQNDSSKELSNVEDLIQQKVDVLLINPVDSDAVVTAIKEANSK 299

NIPVITIDRSANGCDVVSHIASDNVKGGEMAAEPIAKALKQHHH (SEQ ID NO:6)

DNA Sequence:

```
   1 ATGGGTAGCC ACCATCACAA AGGGAACGTC GTGGAATTAG AGGGCATCCC
  51 AGGAGCGTCG GCAGCTCGTG ACCGCGGAAA AGGGTTTGAC GAGGCTATTG
 101 CTAAGTACCC AGACATCAAG ATCGTGGCCA AACAAGCCGC CGACTTTGAT
 151 CGCAGTAAGG GTTTGAGCGT TATGGAAAAC ATCTTACAGG CGCAACCGAA
 201 AATTGATGCA GTGTTCGCGC AAAATGATGA GATGGCTTTG GGTGCAATTA
 251 AAGCAATTGA GGCTGCGAAC CGCCAAGGTA TTATCGTGGT CGGCTTCGAC
 301 GGTACAGAGG ACGCGTTGAA GGCGATTAAA GAAGGGAAGA TGGCGGCGAC
 351 CATTGCACAA CAGCCCGCCT TGATGGGCTC GCTTGGGGTC GAGATGGCTG
 401 ATAAATATCT TAAGGGCGAA AAAATCCCTA ATTTTATCCC CGCTGAATTG
 451 AAATTGATCA CTAAAGAAAA TGTGCAAGGG GGTTCTGCCT CTGGAGGGAC
 501 AAGTGGTGGA TCGAGTGCGG CCGGTTTGGA GGTTTTATTC CAGGGTCCAG
 551 CGGCCGCAGG TGCCCGAGC GGGACCATGG GCTCTGATC CGGTGGCTTA
 601 GAAGTATTAT TCCAAGGTCC AGGTTCGTCA GGAGGGACGG CATCTGGAGG
 651 GAAAGAAGGC AAAACCATCG GTCTGGTCAT CAGTACCTTG AATAACCCCT
 701 TCTTTGTAAC CTTGAAAAAT GGCGCTGAGG AGAAAGCGAA GGAACTGGGA
 751 TACAAGATCA TCGTAGAGGA TTCCCAGAAT GACTCCTCGA AGGAGTTATC
 801 CAACGTTGAG GATTTAATTC AACAGAAGGT CGACGTACTG CTGATTAACC
 851 CTGTAGATTC GGATGCTGTT GTAACCGCCA TTAAGGAAGC AAATAGCAAG
 901 AACATTCCAG TTATTACTAT TGATCGCTCG GCCAACGGGG GTGATGTTGT
 951 TTCCCATATC GCCAGCGATA ATGTTAAGGG TGGCGAAATG GCCGCGGAAT
1001 TTATCGCGAA AGCCCTGAAA GGCCACCATC ACTAA (SEQ ID NO:7)
```

Figure 9B

Split, circularly permuted RBP-clover fusion

Clover amino acid sequence is in boldface. RBP, linkers, MCS, and protease sequences are identical to those above and in non-boldface.

AA sequence of the construct in Fig. 4:

```
MGSHHHKGNVVELEGIPGASAARDRGKGFDEAIAKYPDIKIVAKQAADFD  49
RSKGLSVMENILQAQPKIDAVFAQNDEMALGAIKAIEAANRQGIIVVGFD  99
GTEDALKAIKEGKMAATIAQQPALMGSLGVEMADKYLKGEKIPNFIPAEL 149
KLITKENVQGGSASGGTSGGSSAAGLEVLFQGPAAAGMVSKGEELFTGVV 199
PILVELDGDVNGHKFSVRGEGEGDATNGKLTLKFICTTGKLPVPWPTLVT 249
TFGYGVACFSRYPDHMKQHDFFKSAMPEGYVQERTISFKDDGTYKTRAEV 299
KFEGDTLVNRIELKGIDFKEDGNILGHKLEYNFNSHNVYITADKQKNGIK 349
ANFKIRHNVEDGSVQLADHYQQNTPIGDGPVLLPDNHYLSHQSALSKDPN 399
EKRDHMVLLEFVTAAGITLGMDELYKGSGGLEVLFQGPGSSGGTASGGKE 449
GKTIGLVISTLNNPFFYTLKNGAEEKAKELGYKIIVEDSQNDSSKELSNV 499
EDLIQQKVDVLLINPVDSDAVVTAIKEANSKNIPVITIDRSANGGDVVSH 549
IASDNVKGGEMAAEPIAKALKGHHH* (SEQ ID NO:8)
```

Figure 9B, continued

Other possible RBP circular permutation (CP) sites

AA sequence of RBP (* indicates CP site)

| | | | | | |
|---|---|---|---|---|---|
| MKEGKTIGLV | ISTLNNPFFV | TLKNGAEEKA | KELG*YKIIVE | DSQNDSSKEL | 49 |
| SNVEDLIQQK | *VDVLLINPVD | *SDAVVTAIKE | ANSEN*IPVIT | IDRSANG*GDV | 99 |
| VSHIASDNVK | GGEMAAEFIA | KALKG*KGNVV | ELEGIP*GASA | ARDRGKGFDE | 149 |
| AIAKYPDIKI | VAKQAADFDR | SKGLSVMENI | LQAQPK*IDAV | FAQNDEMALG | 199 |
| AIKAIEAANR | *QGIIVVGFDG | TPDALKAIKE | GKMAATIAQQ | PALMGSLGVE | 249 |
| MADKYLKGEK | IPNPIPAELK | LITKENVQ | (SEQ ID NO:2) | | |

DNA Sequence encoding the above AA sequence

```
  1 ATGAAAGAAG GCAAAACCAT CGGTCTGGTC ATCAGTACCT TGAATAACCC
 51 CTTCTTTGTA ACCTTGAAAA ATGGCGCTGA GGAGAAAGCG AAGGAACTGG
101 GATACAAGAT CATCGTAGAG GATTCCCAGA ATGACTCCTC GAAGGAGTTA
151 TCCAACGTTG AGGATTTAAT TCAACAGAAG GTCGACGTAC TGCTGATTAA
201 CCCTGTAGAT TCGGATGCTG TTGTAACCGC CATTAAGGAA GCAAATAGCA
251 AGAACATTCC AGTTATTACT ATTGATCGCT CGGCCAACGG GGGCGACGTA
301 GTGTCGCATA TCGCAAGCGA TAACGTCAAG GGAGGTGAGA TGGCTGCCGA
351 GTTCATTGCG AAAGCCTTAA AGGGCAAAGG GAACGTCGTG GAATTAGAGG
401 GCATCCCAGG AGCGTCGGCA GCTCGTGACC GCGGAAAAGG GTTTGACGAG
451 GCTATTGCTA AGTACCCAGA CATCAAGATC GTGGCCAAAC AAGCCGCCGA
501 CTTTGATCGC AGTAAGGGTT TGAGCGTTAT GGAAAACATC TTACAGGCGC
551 AACCGAAAAT TGATGCAGTG TTCGCGCAAA ATGATGAGAT GGCTTTGGGT
601 GCAATTAAAG CAATTGAGGC TGCGAACCGC CAAGGTATTA TCGTGGTCGG
651 CTTCGACGGT ACAGAGGACG CGTTGAAGGC GATTAAAGAA GGGAAGATGG
701 CGGCGACCAT TGCACAACAG CCGGCCTTGA TGGGCTCGCT TGGGGTCGAG
751 ATGGCTGATA AATATCTTAA GGGCGAAAAA ATCCCTAATT TTATCCCCGC
801 TGAATTGAAA TTGATCACTA AGAAAATGT GCAATAA (SEQ ID NO:9)
```

Figure 10

AA sequence for pfu MBP:

MKIEEGKVVIWHAMQPNELEVFQSLAEEYMALPEVEIVFEQKPNLEDALK         49

AAIPTGQGPDLFIWAHDWIGKPAEAGLLEPIDEYVTEDLLNEFAPMAQDA         99

MQYKGHYYALPFAAETVAIIYNKEMVSEPPKTFDEMKAIMEKYYDPANEK         149

YGIAWPINAYFISAIAQAPGGYYFDDKTEQPGLDKPETIEGFKFFFTEIW         199

PYMAPTGDYNTQQSIFLEGRAPMMVNGPWSINDVKKAGINFGVVPLPPII         249

KDGKEYWPRPYGGVKLIYFAAGIKNKDAAWKFAKWLTTSEESIKTLALEL         299

GYIPVLTKVLDDPEIKNDPVIYGFGQAVQHAYLMPKSPKMSAVWGGVDGA         349

INEILQDPQNADIEGILKKYQQEILNNMQG (SEQ ID NO:10)

Pful MBP CP126

Legend:

Split Histag 1- (MBP 126-379)- linker 1; TEV protease cleavage site - MCS - Thrombin cleavage site- linker 2 - (MBP 1-125) - split His tag 2

MGSSHHHSSSEPPKTFDEMKAIMEKYYDPANEKYGIAWPINAYFISAIAQ         49

APGGYYFDDKTEQPGLDKPETIEGFKFFFTEIWPYMAPTGDYNTQQSIFL         99

EGRAPMMVNGPWSINDVKKAGINFGVVPLPPIIKDGKEYWPRPYGGVKLI         149

YFAAGIKNKDAAWKFAKWLTTSEESIKTLALELGYIPVLTKVLDDPEIKN         199

DPVIYGFGQAVQHAYLMPKSPKMSAVWGGVDGAINEILQDPQNADIEGIL         249

KKYQQEILNNMQGGGSEASGGTSGGSSAAGENLYFQGAAAGGPSGTMGSGS         299

GGLVPRGSGSSGGTASGGKIEEGKVVIWHAMQPNELEVFQSLAEEYMALP         349

EVEIVFEQKPNLEDALKAAIPTGQGPDLFIWAHDWIGKPAEAGLLEPIDE         399

YVTEDLLNEFAPMAQDAMQYKGHYYALPFAAETVAIIYNKEMVHHH (SEQ ID NO:11)

Figure 11

DNA sequence

```
   1 ATGGGTAGCT CACACCATCA TTCGAGCTCC GAACCACCGA AAACCTTTGA
  51 CGAAATGAAA GCAATCATGG AGAAATACTA CGATCCGGCC AACGAGAAAT
 101 ACGGCATTGC ATGGCCGATT AATGCGTACT TCATTAGCGC CATTGCGCAA
 151 GCGTTCGGAG GTTACTATTT CGATGACAAA ACGGAGCAAC CTGGGTTAGA
 201 TAAACCCGAA ACGATTGAAG GTTTTAAATT CTTCTTTACC GAGATTTGGC
 251 CTTACATGGC TCCTACTGGC GACTATAATA CGCAACAGTC GATCTTTCTG
 301 GAAGGACGTG CTCCGATGAT GGTGAACGGT CCGTGGAGCA TTAACGACGT
 351 CAAGAAAGCC GGCATTAACT TTGGGGTTGT TCCGTTACCG CCGATCATCA
 401 AGCACGGTAA AGAATATTGG CCACGCCCAT ACGGTGGTGT CAAACTGATC
 451 TACTTTGCAG CGGGCATTAA GAACAAAGAT GCCGCGTGGA AATTTGCGAA
 501 ATGGCTGACG ACCTCGGAAG AAAGCATCAA AACATTGGCA CTGGAGTTGG
 551 GCTATATTCC CGTTCTCACT AAGGTACTTG ATGATCCGGA AATTAAGAAC
 601 GATCCGGTAA TTTATGGCTT TGGTCAGGCC GTGCAGCATG CCTATCTGAT
 651 GCCTAAATCT CCCAAAATGT CAGCGGTTTG GGGCGGGGTT GACGGTGCGA
 701 TTAATGAGAT CCTGCAAGAT CCGCAGAATG CCGACATCGA AGGCATCTTG
 751 AAGAAGTATC AGCAGGAAAT TCTGAACAAT ATGCAGGGCG GGGGTTCTGC
 801 CTCTGGAGGG ACAAGTGGTG GATCGAGTGC GGCCGGTGAG AATTTATATT
 851 TTCAGGGTGC GGCCGCAGGT GGCCCGAGCG GGACCATGGG CTCTGGATCC
 901 GGTGGCTTAG TACCGCGCGG TAGCGGTTCG TCAGGAGGGA CGGCATCTGG
 951 AGGGAAAATT GAGGAGGGCA AAGTGGTCAT CTGGCACGCA ATGCAGCCTA
1001 ATGAGCTCGA AGTCTTTCAA AGTCTGGCGG AAGAGTATAT GGCTCTTCCA
1051 GAAGTGGAAA TTGTGTTTGA ACAGAAACCC AATCTGGAAG ATGCGCTTAA
1101 AGCCGCAATT CCAACCGGTC AGGGTCCGGA TCTCTTCATT TGGGCTCATG
1151 ACTGGATTGG CAAATTTGCG GAAGCAGGAC TGCTGGAACC GATCGATGAA
1201 TATGTGACCG AAGATTACT GAACGAATTC GCTCCGATGG CGCAGGATGC
1251 CATGCAATAC AAAGGGCACT ATTATGCGCT GCCGTTCGCT GCAGAGACAG
1301 TGGCCATCAT CTATAACAAA GAAATGGTAC ACCATCACTA A (SEQ ID NO:12)
```

Figure 11, continued

SEQUENCE LISTING

<160> NUMBER OF SEQ ID NOS: 16

<210> SEQ ID NO 1
<211> LENGTH: 277
<212> TYPE: PRT
<213> ORGANISM: Thermoanaerobacter tengcongensis

<400> SEQUENCE: 1

```
Lys Glu Gly Lys Thr Ile Gly Leu Val Ile Ser Thr Leu Asn Asn Pro
1               5                   10                  15

Phe Phe Val Thr Leu Lys Asn Gly Ala Glu Glu Lys Ala Lys Glu Leu
            20                  25                  30

Gly Tyr Lys Ile Ile Val Glu Asp Ser Gln Asn Asp Ser Ser Lys Glu
        35                  40                  45

Leu Ser Asn Val Glu Asp Leu Ile Gln Gln Lys Val Asp Val Leu Leu
    50                  55                  60

Ile Asn Pro Val Asp Ser Asp Ala Val Val Thr Ala Ile Lys Glu Ala
65                  70                  75                  80

Asn Ser Lys Asn Ile Pro Val Ile Thr Ile Asp Arg Ser Ala Asn Gly
                85                  90                  95

Gly Asp Val Val Ser His Ile Ala Ser Asp Asn Val Lys Gly Gly Glu
            100                 105                 110

Met Ala Ala Glu Phe Ile Ala Lys Ala Leu Lys Gly Lys Gly Asn Val
        115                 120                 125

Val Glu Leu Glu Gly Ile Pro Gly Ala Ser Ala Ala Arg Asp Arg Gly
    130                 135                 140

Lys Gly Phe Asp Glu Ala Ile Ala Lys Tyr Pro Asp Ile Lys Ile Val
145                 150                 155                 160

Ala Lys Gln Ala Ala Asp Phe Asp Arg Ser Lys Gly Leu Ser Val Met
                165                 170                 175

Glu Asn Ile Leu Gln Ala Gln Pro Lys Ile Asp Ala Val Phe Ala Gln
            180                 185                 190

Asn Asp Glu Met Ala Leu Gly Ala Ile Lys Ala Ile Glu Ala Ala Asn
        195                 200                 205

Arg Gln Gly Ile Ile Val Val Gly Phe Asp Gly Thr Glu Asp Ala Leu
    210                 215                 220

Lys Ala Ile Lys Glu Gly Lys Met Ala Ala Thr Ile Ala Gln Gln Pro
225                 230                 235                 240

Ala Leu Met Gly Ser Leu Gly Val Glu Met Ala Asp Lys Tyr Leu Lys
                245                 250                 255

Gly Glu Lys Ile Pro Asn Phe Ile Pro Ala Glu Leu Lys Leu Ile Thr
            260                 265                 270

Lys Glu Asn Val Gln
        275
```

<210> SEQ ID NO 2
<211> LENGTH: 278
<212> TYPE: PRT
<213> ORGANISM: Thermoanaerobacter tengocongensis

<400> SEQUENCE: 2

```
Met Lys Glu Gly Lys Thr Ile Gly Leu Val Ile Ser Thr Leu Asn Asn
1               5                   10                  15

Pro Phe Phe Val Thr Leu Lys Asn Gly Ala Glu Glu Lys Ala Lys Glu
            20                  25                  30

Leu Gly Tyr Lys Ile Ile Val Glu Asp Ser Gln Asn Asp Ser Ser Lys
```

```
            35                  40                  45
Glu Leu Ser Asn Val Glu Asp Leu Ile Gln Gln Lys Val Asp Val Leu
         50                  55                  60
Leu Ile Asn Pro Val Asp Ser Asp Ala Val Val Thr Ala Ile Lys Glu
 65                  70                  75                  80
Ala Asn Ser Lys Asn Ile Pro Val Ile Thr Ile Asp Arg Ser Ala Asn
                 85                  90                  95
Gly Gly Asp Val Val Ser His Ile Ala Ser Asp Asn Val Lys Gly Gly
            100                 105                 110
Glu Met Ala Ala Glu Phe Ile Ala Lys Ala Leu Lys Gly Lys Gly Asn
        115                 120                 125
Val Val Glu Leu Glu Gly Ile Pro Gly Ala Ser Ala Ala Arg Asp Arg
    130                 135                 140
Gly Lys Gly Phe Asp Glu Ala Ile Ala Lys Tyr Pro Asp Ile Lys Ile
145                 150                 155                 160
Val Ala Lys Gln Ala Ala Asp Phe Asp Arg Ser Lys Gly Leu Ser Val
                165                 170                 175
Met Glu Asn Ile Leu Gln Ala Gln Pro Lys Ile Asp Ala Val Phe Ala
            180                 185                 190
Gln Asn Asp Glu Met Ala Leu Gly Ala Ile Lys Ala Ile Glu Ala Ala
        195                 200                 205
Asn Arg Gln Gly Ile Ile Val Val Gly Phe Asp Gly Thr Glu Asp Ala
    210                 215                 220
Leu Lys Ala Ile Lys Glu Gly Lys Met Ala Ala Thr Ile Ala Gln Gln
225                 230                 235                 240
Pro Ala Leu Met Gly Ser Leu Gly Val Glu Met Ala Asp Lys Tyr Leu
                245                 250                 255
Lys Gly Glu Lys Ile Pro Asn Phe Ile Pro Ala Glu Leu Lys Leu Ile
            260                 265                 270
Thr Lys Glu Asn Val Gln
        275

<210> SEQ ID NO 3
<211> LENGTH: 353
<212> TYPE: PRT
<213> ORGANISM: Artificial Sequence
<220> FEATURE:
<223> OTHER INFORMATION: Synthetic Sequence

<400> SEQUENCE: 3

Met Gly Ser Ser His His His His His His Ser Ser Gly Asp Val
 1               5                  10                  15
Val Ser His Ile Ala Ser Asp Asn Val Lys Gly Gly Glu Met Ala Ala
                 20                  25                  30
Glu Phe Ile Ala Lys Ala Leu Lys Gly Lys Gly Asn Val Val Glu Leu
            35                  40                  45
Glu Gly Ile Pro Gly Ala Ser Ala Ala Arg Asp Arg Gly Lys Gly Phe
         50                  55                  60
Asp Glu Ala Ile Ala Lys Tyr Pro Asp Ile Lys Ile Val Ala Lys Gln
 65                  70                  75                  80
Ala Ala Asp Phe Asp Arg Ser Lys Gly Leu Ser Val Met Glu Asn Ile
                 85                  90                  95
Leu Gln Ala Gln Pro Lys Ile Asp Ala Val Phe Ala Gln Asn Asp Glu
            100                 105                 110
Met Ala Leu Gly Ala Ile Lys Ala Ile Glu Ala Ala Asn Arg Gln Gly
```

```
                    115                 120                 125
Ile Ile Val Val Gly Phe Asp Gly Thr Glu Asp Ala Leu Lys Ala Ile
        130                 135                 140

Lys Glu Gly Lys Met Ala Ala Thr Ile Ala Gln Gln Pro Ala Leu Met
145                 150                 155                 160

Gly Ser Leu Gly Val Glu Met Ala Asp Lys Tyr Leu Lys Gly Glu Lys
                165                 170                 175

Ile Pro Asn Phe Ile Pro Ala Glu Leu Lys Leu Ile Thr Lys Glu Asn
            180                 185                 190

Val Gln Gly Gly Ser Ala Ser Gly Gly Thr Ser Gly Ser Ser Ala
        195                 200                 205

Ala Gly Leu Glu Val Leu Phe Gln Gly Pro Ala Ala Ala Gly Gly Pro
    210                 215                 220

Ser Gly Thr Met Gly Ser Gly Ser Gly Gly Leu Glu Val Leu Phe Gln
225                 230                 235                 240

Gly Pro Gly Ser Ser Gly Gly Thr Ala Ser Gly Gly Lys Glu Gly Lys
                245                 250                 255

Thr Ile Gly Leu Val Ile Ser Thr Leu Asn Asn Pro Phe Phe Val Thr
            260                 265                 270

Leu Lys Asn Gly Ala Glu Glu Lys Ala Lys Glu Leu Gly Tyr Lys Ile
        275                 280                 285

Ile Val Glu Asp Ser Gln Asn Asp Ser Ser Lys Glu Leu Ser Asn Val
    290                 295                 300

Glu Asp Leu Ile Gln Gln Lys Val Asp Val Leu Leu Ile Asn Pro Val
305                 310                 315                 320

Asp Ser Asp Ala Val Val Thr Ala Ile Lys Glu Ala Asn Ser Lys Asn
                325                 330                 335

Ile Pro Val Ile Thr Ile Asp Arg Ser Ala Asn Gly His His His His
            340                 345                 350

His

<210> SEQ ID NO 4
<211> LENGTH: 1062
<212> TYPE: DNA
<213> ORGANISM: Artificial Sequence
<220> FEATURE:
<223> OTHER INFORMATION: Synthetic sequence

<400> SEQUENCE: 4
atgggtagct cacaccatca ccatcaccat tcgagctcgg gcgacgtagt gtcgcatatc      60
gcaagcgata acgtcaaggg aggtgagatg gctgccgagt tcattgcgaa agccttaaag     120
ggcaaaggga acgtcgtgga attagagggc atcccaggag cgtcggcagc tcgtgaccgc     180
ggaaaagggt ttgacgaggc tattgctaag tacccagaca tcaagatcgt ggccaaacaa     240
gccgccgact tgatcgcag taaggggtttg agcgttatgg aaaacatctt acaggcgcaa     300
ccgaaaattg atgcagtgtt cgcgcaaaat gatgagatgc tttgggtgc aattaaagca     360 attgaggctg cgaaccgcca aggtattatc gtggtcggct cgacggtac agaggacgcg     420 ttgaaggcga ttaagaagg gaagatggcg cgaccattg cacaacagcc ggccttgatg     480
ggctcgcttg gggtcgagat ggctgataaa tatcttaagg gcgaaaaaat ccctaatttt     540
atccccgctg aattgaaatt gatcactaaa gaaaatgtgc aaggggggttc tgcctctgga     600 gggacaagtg tgtgatcgag tgcggccggt ttgagggttt tattccaggg tccagcggcc     660
gcaggtggcc cgagcgggac catgggctct ggatccggtg gcttagaagt attattccaa     720
```

```
ggtccaggtt cgtcaggagg gacggcatct ggagggaaag aaggcaaaac catcggtctg    780
gtcatcagta ccttgaataa ccccttcttt gtaaccttga aaatggcgc tgaggagaaa     840 gcgaaggaac tgggatacaa gatcatcgta gaggattccc agaatgactc ctcgaaggag    900
ttatccaacg ttgaggattt aattcaacag aaggtcgacg tactgctgat taaccctgta    960
gattcggatg ctgttgtaac cgccattaag gaagcaaata gcaagaacat tccagttatt   1020
actattgatc gctcggccaa cgggcaccac caccaccact aa                      1062
```

<210> SEQ ID NO 5
<211> LENGTH: 830
<212> TYPE: PRT
<213> ORGANISM: artificial sequence
<220> FEATURE:
<223> OTHER INFORMATION: recombinant RBP with MDM2

<400> SEQUENCE: 5

```
Met Gly Ser Ser His His His Ser Ser Gly Asp Val Val Ser His
 1               5                  10                  15

Ile Ala Ser Asp Asn Val Lys Gly Gly Glu Met Ala Ala Glu Phe Ile
            20                  25                  30

Ala Lys Ala Leu Lys Gly Lys Gly Asn Val Val Glu Leu Glu Gly Ile
        35                  40                  45

Pro Gly Ala Ser Ala Ala Arg Asp Arg Gly Lys Gly Phe Asp Glu Ala
    50                  55                  60

Ile Ala Lys Tyr Pro Asp Ile Lys Ile Val Ala Lys Gln Ala Ala Asp
65                  70                  75                  80

Phe Asp Arg Ser Lys Gly Leu Ser Val Met Glu Asn Ile Leu Gln Ala
                85                  90                  95

Gln Pro Lys Ile Asp Ala Val Phe Ala Gln Asn Asp Glu Met Ala Leu
            100                 105                 110

Gly Ala Ile Lys Ala Ile Glu Ala Ala Asn Arg Gln Gly Ile Ile Val
        115                 120                 125

Val Gly Phe Asp Gly Thr Glu Asp Ala Leu Lys Ala Ile Lys Glu Gly
    130                 135                 140

Lys Met Ala Ala Thr Ile Ala Gln Gln Pro Ala Leu Met Gly Ser Leu
145                 150                 155                 160

Gly Val Glu Met Ala Asp Lys Tyr Leu Lys Gly Glu Lys Ile Pro Asn
                165                 170                 175

Phe Ile Pro Ala Glu Leu Lys Leu Ile Thr Lys Glu Asn Val Gln Gly
            180                 185                 190

Gly Ser Ala Ser Gly Gly Thr Ser Gly Gly Ser Ala Ala Gly Leu
        195                 200                 205

Glu Val Leu Phe Gln Gly Pro Ala Ala Ala Met Cys Asn Thr Asn Met
    210                 215                 220

Ser Val Pro Thr Asp Gly Ala Val Thr Thr Ser Gln Ile Pro Ala Ser
225                 230                 235                 240

Glu Gln Glu Thr Leu Val Arg Pro Lys Pro Leu Leu Leu Lys Leu Leu
                245                 250                 255

Lys Ser Val Gly Ala Gln Lys Asp Thr Tyr Thr Met Lys Glu Val Leu
            260                 265                 270

Phe Tyr Leu Gly Gln Tyr Ile Met Thr Lys Arg Leu Tyr Asp Glu Lys
        275                 280                 285

Gln Gln His Ile Val Tyr Cys Ser Asn Asp Leu Leu Gly Asp Leu Phe
    290                 295                 300
```

-continued

```
Gly Val Pro Ser Phe Ser Val Lys Glu His Arg Lys Ile Tyr Thr Met
305                 310                 315                 320

Ile Tyr Arg Asn Leu Val Val Asn Gln Gln Ser Ser Asp Ser
            325                 330                 335

Gly Thr Ser Val Ser Glu Asn Arg Cys His Leu Glu Gly Gly Ser Asp
            340                 345                 350

Gln Lys Asp Leu Val Gln Glu Leu Gln Glu Lys Pro Ser Ser Ser
        355                 360                 365

His Leu Val Ser Arg Pro Ser Thr Ser Ser Arg Arg Arg Ala Ile Ser
        370                 375                 380

Glu Thr Glu Glu Asn Ser Asp Glu Leu Ser Gly Glu Arg Gln Arg Lys
385                 390                 395                 400

Arg His Lys Ser Asp Ser Ile Ser Leu Ser Phe Asp Glu Ser Leu Ala
                405                 410                 415

Leu Cys Val Ile Arg Glu Ile Cys Cys Glu Arg Ser Ser Ser Glu
                420                 425                 430

Ser Thr Gly Thr Pro Ser Asn Pro Asp Leu Asp Ala Gly Val Ser Glu
        435                 440                 445

His Ser Gly Asp Trp Leu Asp Gln Asp Ser Val Ser Asp Gln Phe Ser
450                 455                 460

Val Glu Phe Glu Val Glu Ser Leu Asp Ser Glu Asp Tyr Ser Leu Ser
465                 470                 475                 480

Glu Glu Gly Gln Glu Leu Ser Asp Glu Asp Asp Glu Val Tyr Gln Val
                485                 490                 495

Thr Val Tyr Gln Ala Gly Glu Ser Asp Thr Asp Ser Phe Glu Glu Asp
            500                 505                 510

Pro Glu Ile Ser Leu Ala Asp Tyr Trp Lys Cys Thr Ser Cys Asn Glu
            515                 520                 525

Met Asn Pro Pro Leu Pro Ser His Cys Asn Arg Cys Trp Ala Leu Arg
530                 535                 540

Glu Asn Trp Leu Pro Glu Asp Lys Gly Lys Asp Lys Gly Glu Ile Ser
545                 550                 555                 560

Glu Lys Ala Lys Leu Glu Asn Ser Thr Gln Ala Glu Glu Gly Phe Asp
            565                 570                 575

Val Pro Asp Cys Lys Lys Thr Ile Val Asn Asp Ser Arg Glu Ser Cys
            580                 585                 590

Val Glu Glu Asn Asp Asp Lys Ile Thr Gln Ala Ser Gln Ser Gln Glu
        595                 600                 605

Ser Glu Asp Tyr Ser Gln Pro Ser Thr Ser Ser Ser Ile Ile Tyr Ser
        610                 615                 620

Ser Gln Glu Asp Val Lys Glu Phe Glu Arg Glu Glu Thr Gln Asp Lys
625                 630                 635                 640

Glu Glu Ser Val Glu Ser Ser Leu Pro Leu Asn Ala Ile Glu Pro Cys
                645                 650                 655

Val Ile Cys Gln Gly Arg Pro Lys Asn Gly Cys Ile Val His Gly Lys
                660                 665                 670

Thr Gly His Leu Met Ala Cys Phe Thr Cys Ala Lys Lys Leu Lys Lys
        675                 680                 685

Arg Asn Lys Pro Cys Pro Val Cys Arg Gln Pro Ile Gln Met Ile Val
        690                 695                 700

Leu Thr Tyr Phe Pro Gly Ser Gly Gly Leu Glu Val Leu Phe Gln Gly
705                 710                 715                 720
```

Pro Gly Ser Ser Gly Gly Thr Ala Ser Gly Gly Lys Glu Gly Lys Thr
                725                 730                 735

Ile Gly Leu Val Ile Ser Thr Leu Asn Asn Pro Phe Phe Val Thr Leu
            740                 745                 750

Lys Asn Gly Ala Glu Glu Lys Ala Lys Glu Leu Gly Tyr Lys Ile Ile
        755                 760                 765

Val Glu Asp Ser Gln Asn Asp Ser Ser Lys Glu Leu Ser Asn Val Glu
    770                 775                 780

Asp Leu Ile Gln Gln Lys Val Asp Val Leu Leu Ile Asn Pro Val Asp
785                 790                 795                 800

Ser Asp Ala Val Val Thr Ala Ile Lys Glu Ala Asn Ser Lys Asn Ile
                805                 810                 815

Pro Val Ile Thr Ile Asp Arg Ser Ala Asn Gly His His His
            820                 825                 830

<210> SEQ ID NO 6
<211> LENGTH: 344
<212> TYPE: PRT
<213> ORGANISM: Artificial Sequence
<220> FEATURE:
<223> OTHER INFORMATION: recombinant polypeptide

<400> SEQUENCE: 6

Met Gly Ser His His His Lys Gly Asn Val Val Glu Leu Glu Gly Ile
1               5                   10                  15

Pro Gly Ala Ser Ala Ala Arg Asp Arg Gly Lys Gly Phe Asp Glu Ala
            20                  25                  30

Ile Ala Lys Tyr Pro Asp Ile Lys Ile Val Ala Lys Gln Ala Ala Asp
        35                  40                  45

Phe Asp Arg Ser Lys Gly Leu Ser Val Met Glu Asn Ile Leu Gln Ala
    50                  55                  60

Gln Pro Lys Ile Asp Ala Val Phe Ala Gln Asn Asp Glu Met Ala Leu
65                  70                  75                  80

Gly Ala Ile Lys Ala Ile Glu Ala Ala Asn Arg Gln Gly Ile Ile Val
                85                  90                  95

Val Gly Phe Asp Gly Thr Glu Asp Ala Leu Lys Ala Ile Lys Glu Gly
            100                 105                 110

Lys Met Ala Ala Thr Ile Ala Gln Gln Pro Ala Leu Met Gly Ser Leu
        115                 120                 125

Gly Val Glu Met Ala Asp Lys Tyr Leu Lys Gly Glu Lys Ile Pro Asn
    130                 135                 140

Phe Ile Pro Ala Glu Leu Lys Leu Ile Thr Lys Glu Asn Val Gln Gly
145                 150                 155                 160

Gly Ser Ala Ser Gly Gly Thr Ser Gly Gly Ser Ser Ala Ala Gly Leu
                165                 170                 175

Glu Val Leu Phe Gln Gly Pro Ala Ala Ala Gly Gly Pro Ser Gly Thr
            180                 185                 190

Met Gly Ser Gly Ser Gly Gly Leu Glu Val Leu Phe Gln Gly Pro Gly
        195                 200                 205

Ser Ser Gly Gly Thr Ala Ser Gly Gly Lys Glu Gly Lys Thr Ile Gly
    210                 215                 220

Leu Val Ile Ser Thr Leu Asn Asn Pro Phe Phe Val Thr Leu Lys Asn
225                 230                 235                 240

Gly Ala Glu Glu Lys Ala Lys Glu Leu Gly Tyr Lys Ile Ile Val Glu
                245                 250                 255

```
Asp Ser Gln Asn Asp Ser Ser Lys Glu Leu Ser Asn Val Glu Asp Leu
                260                 265                 270

Ile Gln Gln Lys Val Asp Val Leu Leu Ile Asn Pro Val Asp Ser Asp
            275                 280                 285

Ala Val Val Thr Ala Ile Lys Glu Ala Asn Ser Lys Asn Ile Pro Val
        290                 295                 300

Ile Thr Ile Asp Arg Ser Ala Asn Gly Gly Asp Val Val Ser His Ile
305                 310                 315                 320

Ala Ser Asp Asn Val Lys Gly Gly Glu Met Ala Ala Glu Phe Ile Ala
                325                 330                 335

Lys Ala Leu Lys Gly His His His
            340
```

<210> SEQ ID NO 7
<211> LENGTH: 1035
<212> TYPE: DNA
<213> ORGANISM: artificial sequence
<220> FEATURE:
<223> OTHER INFORMATION: synthetic sequence

<400> SEQUENCE: 7

```
atgggtagcc accatcacaa agggaacgtc gtggaattag agggcatccc aggagcgtcg    60
gcagctcgtg accgcggaaa agggtttgac gaggctattg ctaagtaccc agacatcaag   120
atcgtggcca acaagccgcc gactttgat cgcagtaagg gtttgagcgt tatggaaaac   180
atcttacagg cgcaaccgaa aattgatgca gtgttcgcgc aaaatgatga gatggctttg   240
ggtgcaatta aagcaattga ggctgcgaac cgccaaggta ttatcgtggt cggcttcgac   300
ggtacagagg acgcgttgaa ggcgattaaa gaagggaaga tggcggcgac cattgcacaa   360
cagccggcct tgatgggctc gcttggggtc gagatggctg ataaatatct taagggcgaa   420
aaaatcccta attttatccc cgctgaattg aaattgatca ctaaagaaaa tgtgcaaggg   480
ggttctgcct ctggagggac aagtggtgga tcgagtgcgg ccggtttgga ggttttattc   540
cagggtccag cggccgcagg tggcccgagc gggaccatgg ctctggatc cggtggctta   600
gaagtattat tccaaggtcc aggttcgtca ggagggacgg catctggagg aaagaaggc   660
aaaaccatcg gtctggtcat cagtaccttg aataacccct ctttgtaac cttgaaaaat   720
ggcgctgagg agaaagcgaa ggaactggga tacaagatca tcgtagagga ttcccagaat   780
gactcctcga aggagttatc caacgttgag gatttaattc aacagaaggt cgacgtactg   840
ctgattaacc ctgtagattc ggatgctgtt gtaaccgcca ttaaggaagc aaatagcaag   900
aacattccag ttattactat tgatcgctcg gccaacgggg gtgatgttgt tcccatatc   960
gccagcgata atgttaaggg tggcgaaatg gccgcggaat ttatcgcgaa agccctgaaa  1020
ggccaccatc actaa                                                    1035
```

<210> SEQ ID NO 8
<211> LENGTH: 575
<212> TYPE: PRT
<213> ORGANISM: Artificial Sequence
<220> FEATURE:
<223> OTHER INFORMATION: Synthetic sequence

<400> SEQUENCE: 8

```
Met Gly Ser His His His Lys Gly Asn Val Val Glu Leu Glu Gly Ile
1               5                   10                  15

Pro Gly Ala Ser Ala Ala Arg Asp Arg Gly Lys Gly Phe Asp Glu Ala
            20                  25                  30
```

-continued

```
Ile Ala Lys Tyr Pro Asp Ile Lys Ile Val Ala Lys Gln Ala Ala Asp
         35                  40                  45
Phe Asp Arg Ser Lys Gly Leu Ser Val Met Glu Asn Ile Leu Gln Ala
 50                  55                  60
Gln Pro Lys Ile Asp Ala Val Phe Ala Gln Asn Asp Glu Met Ala Leu
 65                  70                  75                  80
Gly Ala Ile Lys Ala Ile Glu Ala Ala Asn Arg Gln Gly Ile Ile Val
                 85                  90                  95
Val Gly Phe Asp Gly Thr Glu Asp Ala Leu Lys Ala Ile Lys Glu Gly
                100                 105                 110
Lys Met Ala Ala Thr Ile Ala Gln Gln Pro Ala Leu Met Gly Ser Leu
                115                 120                 125
Gly Val Glu Met Ala Asp Lys Tyr Leu Lys Gly Glu Lys Ile Pro Asn
            130                 135                 140
Phe Ile Pro Ala Glu Leu Lys Leu Ile Thr Lys Glu Asn Val Gln Gly
145                 150                 155                 160
Gly Ser Ala Ser Gly Gly Thr Ser Gly Gly Ser Ala Ala Gly Leu
                    165                 170                 175
Glu Val Leu Phe Gln Gly Pro Ala Ala Ala Gly Met Val Ser Lys Gly
                180                 185                 190
Glu Glu Leu Phe Thr Gly Val Val Pro Ile Leu Val Glu Leu Asp Gly
                195                 200                 205
Asp Val Asn Gly His Lys Phe Ser Val Arg Gly Glu Gly Glu Gly Asp
210                 215                 220
Ala Thr Asn Gly Lys Leu Thr Leu Lys Phe Ile Cys Thr Thr Gly Lys
225                 230                 235                 240
Leu Pro Val Pro Trp Pro Thr Leu Val Thr Thr Phe Gly Tyr Gly Val
                245                 250                 255
Ala Cys Phe Ser Arg Tyr Pro Asp His Met Lys Gln His Asp Phe Phe
                260                 265                 270
Lys Ser Ala Met Pro Glu Gly Tyr Val Gln Glu Arg Thr Ile Ser Phe
            275                 280                 285
Lys Asp Asp Gly Thr Tyr Lys Thr Arg Ala Glu Val Lys Phe Glu Gly
290                 295                 300
Asp Thr Leu Val Asn Arg Ile Glu Leu Lys Gly Ile Asp Phe Lys Glu
305                 310                 315                 320
Asp Gly Asn Ile Leu Gly His Lys Leu Glu Tyr Asn Phe Asn Ser His
                325                 330                 335
Asn Val Tyr Ile Thr Ala Asp Lys Gln Lys Asn Gly Ile Lys Ala Asn
                340                 345                 350
Phe Lys Ile Arg His Asn Val Glu Asp Gly Ser Val Gln Leu Ala Asp
            355                 360                 365
His Tyr Gln Gln Asn Thr Pro Ile Gly Asp Gly Pro Val Leu Leu Pro
        370                 375                 380
Asp Asn His Tyr Leu Ser His Gln Ser Ala Leu Ser Lys Asp Pro Asn
385                 390                 395                 400
Glu Lys Arg Asp His Met Val Leu Leu Glu Phe Val Thr Ala Ala Gly
                405                 410                 415
Ile Thr Leu Gly Met Asp Glu Leu Tyr Lys Gly Ser Gly Gly Leu Glu
                420                 425                 430
Val Leu Phe Gln Gly Pro Gly Ser Ser Gly Gly Thr Ala Ser Gly Gly
            435                 440                 445
```

Lys Glu Gly Lys Thr Ile Gly Leu Val Ile Ser Thr Leu Asn Asn Pro
            450                 455                 460

Phe Phe Val Thr Leu Lys Asn Gly Ala Glu Glu Lys Ala Lys Glu Leu
465                 470                 475                 480

Gly Tyr Lys Ile Ile Val Glu Asp Ser Gln Asn Asp Ser Ser Lys Glu
                485                 490                 495

Leu Ser Asn Val Glu Asp Leu Ile Gln Gln Lys Val Asp Val Leu Leu
            500                 505                 510

Ile Asn Pro Val Asp Ser Asp Ala Val Val Thr Ala Ile Lys Glu Ala
            515                 520                 525

Asn Ser Lys Asn Ile Pro Val Ile Thr Ile Asp Arg Ser Ala Asn Gly
530                 535                 540

Gly Asp Val Val Ser His Ile Ala Ser Asp Asn Val Lys Gly Gly Glu
545                 550                 555                 560

Met Ala Ala Glu Phe Ile Ala Lys Ala Leu Lys Gly His His His
                565                 570                 575

<210> SEQ ID NO 9
<211> LENGTH: 837
<212> TYPE: DNA
<213> ORGANISM: Artificial Sequence
<220> FEATURE:
<223> OTHER INFORMATION: DNA sequence encoding RBP with CP sites

<400> SEQUENCE: 9
atgaaagaag gcaaaaccat cggtctggtc atcagtacct tgaataaccc cttctttgta      60
accttgaaaa atggcgctga ggagaaagcg aaggaactgg atacaagat catcgtagag      120 gattcccaga tgactcctc gaaggagtta ccaacgttg aggatttaat tcaacagaag      180
gtcgacgtac tgctgattaa ccctgtagat tcggatgctg ttgtaaccgc cattaaggaa      240
gcaaatagca agaacattcc agttattact attgatcgct cggccaacgg gggcgacgta      300
gtgtcgcata tcgcaagcga taacgtcaag ggaggtgaga tggctgccga gttcattgcg      360
aaagccttaa agggcaaagg gaacgtcgtg gaattagagg gcatcccagg agcgtcggca      420
gctcgtgacc gcggaaaagg gtttgacgag gctattgcta agtacccaga catcaagatc      480
gtggccaaac aagccgccga ctttgatcgc agtaagggtt tgagcgttat ggaaaacatc      540
ttacaggcgc aaccgaaaat tgatgcagtg ttcgcgcaaa atgatgagat ggcttggggt      600
gcaattaaag caattgaggc tgcgaaccgc caaggtatta tcgtggtcgg cttcgacggt      660
acagaggacg cgttgaaggc gattaaagaa gggaagatgg cggcgaccat tgcacaacag      720
ccggccttga tgggctcgct tggggtcgag atggctgata aatatcttaa gggcgaaaaa      780
atccctaatt ttatccccgc tgaattgaaa ttgatcacta agaaaatgt gcaataa         837

<210> SEQ ID NO 10
<211> LENGTH: 380
<212> TYPE: PRT
<213> ORGANISM: Pyrococcus furiosus

<400> SEQUENCE: 10

Met Lys Ile Glu Glu Gly Lys Val Val Ile Trp His Ala Met Gln Pro
1               5                   10                  15

Asn Glu Leu Glu Val Phe Gln Ser Leu Ala Glu Glu Tyr Met Ala Leu
            20                  25                  30

Pro Glu Val Glu Ile Val Phe Glu Gln Lys Pro Asn Leu Glu Asp Ala
        35                  40                  45

```
Leu Lys Ala Ala Ile Pro Thr Gly Gln Gly Pro Asp Leu Phe Ile Trp
 50                  55                  60

Ala His Asp Trp Ile Gly Lys Phe Ala Glu Ala Gly Leu Leu Glu Pro
 65                  70                  75                  80

Ile Asp Glu Tyr Val Thr Glu Asp Leu Leu Asn Glu Phe Ala Pro Met
                 85                  90                  95

Ala Gln Asp Ala Met Gln Tyr Lys Gly His Tyr Tyr Ala Leu Pro Phe
            100                 105                 110

Ala Ala Glu Thr Val Ala Ile Ile Tyr Asn Lys Glu Met Val Ser Glu
            115                 120                 125

Pro Pro Lys Thr Phe Asp Glu Met Lys Ala Ile Met Glu Lys Tyr Tyr
130                 135                 140

Asp Pro Ala Asn Glu Lys Tyr Gly Ile Ala Trp Pro Ile Asn Ala Tyr
145                 150                 155                 160

Phe Ile Ser Ala Ile Ala Gln Ala Phe Gly Gly Tyr Tyr Phe Asp Asp
                165                 170                 175

Lys Thr Glu Gln Pro Gly Leu Asp Lys Pro Glu Thr Ile Glu Gly Phe
            180                 185                 190

Lys Phe Phe Thr Glu Ile Trp Pro Tyr Met Ala Pro Thr Gly Asp
            195                 200                 205

Tyr Asn Thr Gln Gln Ser Ile Phe Leu Glu Gly Arg Ala Pro Met Met
210                 215                 220

Val Asn Gly Pro Trp Ser Ile Asn Asp Val Lys Ala Gly Ile Asn
225                 230                 235                 240

Phe Gly Val Val Pro Leu Pro Ile Ile Lys Asp Gly Lys Glu Tyr
                245                 250                 255

Trp Pro Arg Pro Tyr Gly Gly Val Lys Leu Ile Tyr Phe Ala Ala Gly
            260                 265                 270

Ile Lys Asn Lys Asp Ala Ala Trp Lys Phe Ala Lys Trp Leu Thr Thr
            275                 280                 285

Ser Glu Glu Ser Ile Lys Thr Leu Ala Leu Glu Leu Gly Tyr Ile Pro
            290                 295                 300

Val Leu Thr Lys Val Leu Asp Asp Pro Glu Ile Lys Asn Asp Pro Val
305                 310                 315                 320

Ile Tyr Gly Phe Gly Gln Ala Val Gln His Ala Tyr Leu Met Pro Lys
                325                 330                 335

Ser Pro Lys Met Ser Ala Val Trp Gly Val Asp Gly Ala Ile Asn
            340                 345                 350

Glu Ile Leu Gln Asp Pro Gln Asn Ala Asp Ile Glu Gly Ile Leu Lys
            355                 360                 365

Lys Tyr Gln Gln Glu Ile Leu Asn Asn Met Gln Gly
370                 375                 380

<210> SEQ ID NO 11
<211> LENGTH: 446
<212> TYPE: PRT
<213> ORGANISM: Artificial Sequence
<220> FEATURE:
<223> OTHER INFORMATION: PfuI permutated polypeptide

<400> SEQUENCE: 11

Met Gly Ser Ser His His His Ser Ser Glu Pro Pro Lys Thr Phe
1               5                   10                  15

Asp Glu Met Lys Ala Ile Met Glu Lys Tyr Tyr Asp Pro Ala Asn Glu
                20                  25                  30
```

-continued

```
Lys Tyr Gly Ile Ala Trp Pro Ile Asn Ala Tyr Phe Ile Ser Ala Ile
             35                  40                  45

Ala Gln Ala Phe Gly Gly Tyr Tyr Phe Asp Asp Lys Thr Glu Gln Pro
 50                  55                  60

Gly Leu Asp Lys Pro Glu Thr Ile Glu Gly Phe Lys Phe Phe Phe Thr
 65                  70                  75                  80

Glu Ile Trp Pro Tyr Met Ala Pro Thr Gly Asp Tyr Asn Thr Gln Gln
                     85                  90                  95

Ser Ile Phe Leu Glu Gly Arg Ala Pro Met Met Val Asn Gly Pro Trp
                100                 105                 110

Ser Ile Asn Asp Val Lys Lys Ala Gly Ile Asn Phe Gly Val Val Pro
                115                 120                 125

Leu Pro Pro Ile Ile Lys Asp Gly Lys Glu Tyr Trp Pro Arg Pro Tyr
130                 135                 140

Gly Gly Val Lys Leu Ile Tyr Phe Ala Ala Gly Ile Lys Asn Lys Asp
145                 150                 155                 160

Ala Ala Trp Lys Phe Ala Lys Trp Leu Thr Thr Ser Glu Glu Ser Ile
                165                 170                 175

Lys Thr Leu Ala Leu Glu Leu Gly Tyr Ile Pro Val Leu Thr Lys Val
                180                 185                 190

Leu Asp Asp Pro Glu Ile Lys Asn Asp Pro Val Ile Tyr Gly Phe Gly
                195                 200                 205

Gln Ala Val Gln His Ala Tyr Leu Met Pro Lys Ser Pro Lys Met Ser
210                 215                 220

Ala Val Trp Gly Gly Val Asp Gly Ala Ile Asn Glu Ile Leu Gln Asp
225                 230                 235                 240

Pro Gln Asn Ala Asp Ile Glu Gly Ile Leu Lys Lys Tyr Gln Gln Glu
                245                 250                 255

Ile Leu Asn Asn Met Gln Gly Gly Ser Ala Ser Gly Gly Thr Ser
                260                 265                 270

Gly Gly Ser Ser Ala Ala Gly Glu Asn Leu Tyr Phe Gln Gly Ala Ala
                275                 280                 285

Ala Gly Gly Pro Ser Gly Thr Met Gly Ser Gly Ser Gly Gly Leu Val
290                 295                 300

Pro Arg Gly Ser Gly Ser Ser Gly Gly Thr Ala Ser Gly Gly Lys Ile
305                 310                 315                 320

Glu Glu Gly Lys Val Val Ile Trp His Ala Met Gln Pro Asn Glu Leu
                325                 330                 335

Glu Val Phe Gln Ser Leu Ala Glu Glu Tyr Met Ala Leu Pro Glu Val
                340                 345                 350

Glu Ile Val Phe Glu Gln Lys Pro Asn Leu Glu Asp Ala Leu Lys Ala
                355                 360                 365

Ala Ile Pro Thr Gly Gln Gly Pro Asp Leu Phe Ile Trp Ala His Asp
370                 375                 380

Trp Ile Gly Lys Phe Ala Glu Ala Gly Leu Leu Glu Pro Ile Asp Glu
385                 390                 395                 400

Tyr Val Thr Glu Asp Leu Leu Asn Glu Phe Ala Pro Met Ala Gln Asp
                405                 410                 415

Ala Met Gln Tyr Lys Gly His Tyr Tyr Ala Leu Pro Phe Ala Ala Glu
                420                 425                 430

Thr Val Ala Ile Ile Tyr Asn Lys Glu Met Val His His His
                435                 440                 445
```

<210> SEQ ID NO 12
<211> LENGTH: 1341
<212> TYPE: DNA
<213> ORGANISM: artificial sequence
<220> FEATURE:
<223> OTHER INFORMATION: synthetic sequence

<400> SEQUENCE: 12

```
atgggtagct cacaccatca ttcgagctcc gaaccaccga aaacctttga cgaaatgaaa      60
gcaatcatgg agaaatacta cgatccggcc aacgagaaat acggcattgc atggccgatt     120
aatgcgtact tcattagcgc cattgcgcaa gcgttcggag gttactattt cgatgacaaa     180
acggagcaac ctgggttaga taaacccgaa acgattgaag ttttaaatt cttctttacc      240
gagatttggc cttacatggc tcctactggc gactataata cgcaacagtc gatctttctg     300
gaaggacgtg ctccgatgat ggtgaacggt ccgtggagca ttaacgacgt caagaaagcc     360
ggcattaact ttgggggttgt tccgttaccg ccgatcatca aggacggtaa agaatattgg     420
ccacgcccat acggtggtgt caaactgatc tactttgcag cgggcattaa gaacaaagat     480
gccgcgtgga aatttgcgaa atggctgacc acctcggaag aaagcatcaa acattggca     540
ctggagttgg gctatattcc cgttctcact aaggtacttg atgatccgga attaagaac     600
gatccggtaa tttatggctt tggtcaggcc gtgcagcatg cctatctgat gcctaaatct     660
cccaaaatgt cagcggtttg gggcggggtt gacggtgcga ttaatgagat cctgcaagat     720
ccgcagaatg ccgacatcga aggcatcttg aagaagtatc agcaggaaat tctgaacaat     780
atgcagggcg ggggttctgc ctctggaggg acaagtggtg gatcgagtgc ggccggtgag     840
aatttatatt ttcagggtgc ggccgcaggt ggcccgagcg ggaccatggg ctctggatcc     900
ggtggcttag taccgcgcgg tagcggttcg tcaggaggga cggcatctgg agggaaaatt     960
gaggagggca aagtggtcat ctggcacgca atgcagccta atgagctcga agtcttcaa    1020
agtctggcgg aagagtatat ggctcttcca gaagtggaaa ttgtgtttga acagaaaccc    1080
aatctggaag atgcgcttaa agccgcaatt ccaaccggtc agggtccgga tctcttcatt    1140
tgggctcatg actggattgg caaatttgcg gaagcaggac tgctggaacc gatcgatgaa    1200
tatgtgaccg aagatttact gaacgaattc gctccgatgg cgcaggatgc catgcaatac    1260
aaagggcact attatgcgct gccgttcgct gcagagacag tggccatcat ctataacaaa    1320
gaaatggtac accatcacta a                                              1341
```

<210> SEQ ID NO 13
<211> LENGTH: 7
<212> TYPE: PRT
<213> ORGANISM: artificial sequence
<220> FEATURE:
<223> OTHER INFORMATION: synthetic sequence

<400> SEQUENCE: 13

Glu Asn Leu Tyr Phe Gln Gly
1               5

<210> SEQ ID NO 14
<211> LENGTH: 5
<212> TYPE: PRT
<213> ORGANISM: artificial sequence
<220> FEATURE:
<223> OTHER INFORMATION: synthetic sequence

<400> SEQUENCE: 14

Asp Asp Asp Asp Lys

<210> SEQ ID NO 15
<211> LENGTH: 4
<212> TYPE: PRT
<213> ORGANISM: artificial sequence
<220> FEATURE:
<223> OTHER INFORMATION: synthetic sequence

<400> SEQUENCE: 15

Ile Glu Gly Arg
1

<210> SEQ ID NO 16
<211> LENGTH: 6
<212> TYPE: PRT
<213> ORGANISM: artificial sequence
<220> FEATURE:
<223> OTHER INFORMATION: synthetic sequence

<400> SEQUENCE: 16

Leu Val Pro Arg Gly Ser
1               5

COMPOSITIONS AND METHODS COMPRISING PERMUTED PROTEIN TAGS FOR FACILITATING OVEREXPRESSION, SOLUBILITY, AND PURIFICATION OF TARGET PROTEINS

CROSS REFERENCE TO RELATED APPLICATIONS

This application claims priority to U.S. provisional patent application No. 62/411,295, filed Oct. 21, 2016, and to U.S. provisional patent application No. 62/518,207, filed Jun. 12, 2017, the disclosures of each of which are incorporated herein by reference.

GOVERNMENT SUPPORT CLAUSE

This invention was made with government support under grant no. GM069755 and GM115762 awarded by the National Institutes of Health. The government has certain rights in the invention.

INCORPORATION OF THE SEQUENCE LISTING

The present application contains a sequence listing the content of which is hereby incorporated by reference.

BACKGROUND

There is an ongoing and unmet need for compositions and methods that improve expression, solubility and/or purification of proteins. The present disclosure pertains to these needs.

SUMMARY

The present disclosure provides improved compositions and methods for expressing proteins. In embodiments the disclosure provides expression vectors that are suitable for expressing target proteins that are present in fusion proteins between separate segments of Ribose Binding Protein (RBP) or Maltose Binding Protein (MBP). Kits comprising the expression vectors and cells comprising the expression vectors are included. Methods of making fusion proteins, methods of separating fusion proteins and/or the target proteins they include are also included, as are the fusion proteins themselves.

In particular embodiments the disclosure provides an expression vector encoding a polypeptide, the polypeptide comprising sequentially in an N to C terminal direction:

a) optionally, at the N-terminus of the polypeptide a first Histidine sequence that can function as a component of a functional Histidine tag with a second Histidine sequence located at the C-terminus of the polypeptide;

b) a first segment of a Ribose Binding Protein (RBP);

c) a first linker sequence;

d) at least one restriction endonuclease digestion site;

e) a second linker sequence;

f) a second segment of the RBP.

In one embodiment the second segment is located N-terminal to the first segment relative to an intact wild type amino acid sequence of an RBP comprising the sequence of SEQ ID NO:1, and the sequence is permuted as further described herein, but the disclosure includes non-permuted configurations as well, and thus includes permuted and linear version of the fusion proteins. The expression vector optionally further encodes at the C-terminus of the polypeptide a second Histidine sequence that can function with the first Histidine sequence in the functional Histidine tag, wherein the functional His tag may have improved metal binding relative to either of the first or second His tags alone.

Proteins described herein can comprise a non-covalently bound ribose, which can be present in cells that make the proteins, and which may persist during separation of the protein from the cells if such separation is performed.

In a configuration of the first and second segments, the amino acid sequence of the first segment and the amino acid sequence of the second segment together comprise an amino acid sequence that has at least 90% identity with a segment of SEQ ID NO:1 that is at least 251 amino acids in length, and the amino acid sequences of the first and second segments do not overlap with each other. This degree of identity includes amino acid sequences that have, for example, insertions and/or deletions (gaps), or amino acid substitutions/mutations. In one implementation the first and second segments can together have at least 90% identity with a segment of SEQ ID NO:1 that comprises amino acids number 4 and 254 of SEQ ID NO:1.

In an embodiment the configuration is such that the first linker and the second linker, and the first protease cleavage site if present, and the second protease cleavage site if present, together comprise at least thirty amino acids. If present cleavage sites can be the same or different from each other. In embodiments, the fusion proteins can comprises sequences such that they are susceptible to non-enzymatic cleavage, which can be used in conjunction with or as an alternative to protease recognition sites.

In certain embodiments the segment of SEQ ID NO:1 is amino acids 4-254 of SEQ NO:1. In embodiments, the second segment comprises a contiguous amino acid sequence that has at least 90% identity with a segment of SEQ ID NO:1 that begins with amino acid number 1, 2, 3, or 4 of SEQ ID NO:1 and ends with amino acid number 33, 59, 69, 84, 96, 124, 135, 185, or 209 of SEQ ID NO:1 In embodiments, the first segment comprises a contiguous amino acid sequence that has at least 90% identity with a segment of SEQ ID NO:1 that is amino acids 34-254 of SEQ ID NO:1, 60-254 of SEQ ID NO:1, 70-254 of SEQ ID NO:1, 85-254 of SEQ ID NO:1, 97-254 of SEQ ID NO:1, 125-254 of SEQ ID NO:1, 136-254 of SEQ ID NO:1, 186-254 of SEQ ID NO:1, or 210-254 of SEQ ID NO:1, thereby having the first amino acid of the first segment as amino acid 34, 60, 70, 85, 97, 125, 136, 186 or 210 of SEQ ID NO:1, and wherein the first segment is optionally extended by any number of amino acids up to amino acid number 277 of SEQ ID NO:1. In one embodiment the first segment ends at amino acid 277 of SEQ ID NO:1.

In certain embodiments the second segment comprises a contiguous amino acid sequence of SEQ ID NO:1 that begins with amino acid number 1, 2, 3, or 4 of SEQ ID NO:1 and ends with amino acid number 33, 59, 69, 84, 96, 124, 135, 185, or 209 of SEQ ID NO:1. In one embodiment, the second segment ends at amino acid 96 or amino acid 124 of SEQ ID NO:1.

In certain embodiments, the expression vector has at least one restriction endonuclease digestion present in a multiple cloning site; and/or ii) the expression vector further encodes at least one protease cleavage site located between the at least one restriction endonuclease digestion site and the first or the second linker sequence; and/or iii) the first and/or the second linker is at least 15 amino acids in length. In one approach at least one restriction endonuclease digestion site is present in the multiple cloning site and the first and/or the second linker is at least 15 amino acids in length.

In another aspect the disclosure comprises methods. In one approach the method comprises allowing expression of any expression vector described herein such that a fusion protein is expressed, with the proviso that a polynucleotide sequence encoding a target protein is inserted into the multiple cloning site, and wherein the expressed fusion protein optionally comprises the first and second Histidine sequences, the first and second segments of the Ribose Binding Protein, the first and second linker sequences, and the at least one protease cleavage site if the protease cleavage site is encoded by the expression vector. In embodiments, the protein comprises one or both of the Histidine sequences, and the method further comprises exposing the fusion protein to a metal such that the first and second Histidine sequences form a functional Histidine tag that forms a non-covalent association with the metal. The method can further comprise separating the fusion protein from the metal. In certain approaches the fusion protein comprises at least one protease cleavage site and optionally comprises a second protease cleavage site such that the first and second protease cleavage sites flank the target protein. In an embodiment the method further comprising cleaving the fusion protein at the first or the first and the second protease cleavage sites, and optionally purifying a protein cleavage product that comprises the target protein.

In certain aspects the disclosure includes expressing the fusion proteins in prokaryotic or eukaryotic cells, and includes such cells and cell cultures, and cell culture media. In embodiments, kits comprising the expression vectors are provided.

BRIEF DESCRIPTION OF THE FIGURES

(FIG. 1, panel A). The endonuclease site (ERS) is intact before the sequence encoding Target protein is inserted into the expression vector. The ERS can be present in a multi-cloning site in an expression vector that contains a plurality of endonuclease recognition sites (i.e., restriction sites).

FIG. 2 provides a schematic of representative fusion proteins. Panel A, linear tag, similar to FIG. 1, Panel A. FIG. 2 Panel B, split His tag with linear permutated Ribose Binding Protein (RBP). Panel C, linear RBP tag with a target protein inserted in between positions 96 and 97 of RBP flanked by linker sequences (circular RBP tag). FIG. 2C accordingly shows that in contrast to the split, circularly-permuted tag of this disclosure (using RBP as a representative solubility tag), the target protein gene can be inserted internally into the RBP gene, and thus can be used to produce a fusion protein encoded by the gene with the same protein orientation.

FIG. 9A provides the amino acid and DNA sequences of a split tteRBP protein (s97) with a multiple cloning site for inserting a target gene (with N-terminal Met) and two linker sequences. tteRBP is *Thermoanaerobacter tengcongensis* (tte) RBP.

FIG. 9B provides the amino acid sequence of a split, circularly permuted RBP-MDM2 fusion protein, the sequence of a split tteRBP protein (s125) with a multiple cloning site for inserting a target gene, and a split, circularly permuted RBP-clove fusion. FIG. 9B also provides the amino acid sequence of a split, circularly permuted RBP-MDM2 fusion protein, the sequence of a split tteRBP protein with a multiple cloning site for inserting a target gene, and a split, circularly permuted RBP-clove fusion.

FIG. 10 provides the amino acid sequence of tteRBP with permutation sites signified by asterisks.

FIG. 11 provides the amino acid sequence of *Pyrococcus furiosus* (pfu) MPB, and the amino acid and DNA sequences of a split pfu MBP protein with a multiple cloning site for inserting a target gene. Pfu is extremophilic species of Archaea.

DETAILED DESCRIPTION

Figure 1:
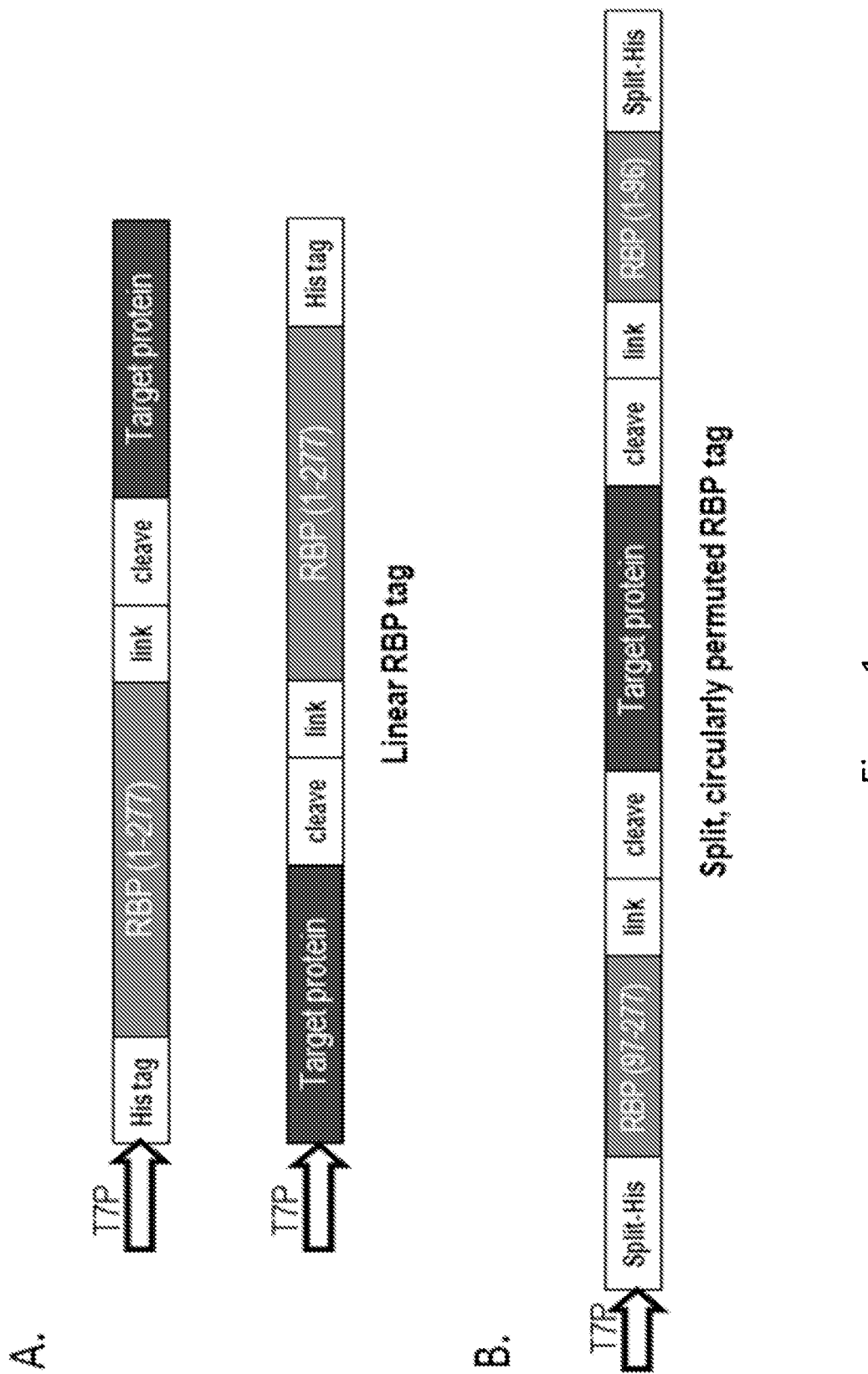
FIG. 1 provides a schematic comparisons of embodiments of this disclosure (FIG. 1, panel B) with linear tags, such as are described in PCT/US16/56832.

Unless defined otherwise herein, all technical and scientific terms used in this disclosure have the same meaning as commonly understood by one of ordinary skill in the art to which this disclosure pertains.

Every numerical range given throughout this specification includes its upper and lower values, as well as every narrower numerical range that falls within it, as if such narrower numerical ranges were all expressly written herein. Every DNA sequence disclosed herein includes its complementary DNA sequence, and also includes the RNA equivalents thereof. Every DNA and RNA sequence encoding the polypeptides disclosed herein is encompassed by this disclosure, including but not limited to all fusion proteins, and all of the Ribose Binding Protein (RBP) segment of fusion proteins and all of the Maltose Binding Protein (MBP) segment of fusion proteins, including but not limited to those comprising N-terminal and/or C-terminal truncations of the RBP segment or the MBP segment.

The disclosure includes permuted and non-permuted protein configurations of proteins, which can be present in fusion proteins. "Permuted" and "permutation" and "permuting" and "permute" and "permutants" as used herein means that, relative to a wild type amino reference sequence, proteins of this disclosure have first and second segments of an RBP or MBP, wherein the second segment is located N-terminal to the first segment when compared to an intact wild type amino acid sequence of the RBP of the MBP. To illustrate in a non-limiting fashion, a hypothetical contiguous reference protein has a series of segments of $NH_2$-$AA_1$ $AA_2$, $AA_3$, $AA_4$, $AA_5$, $AA_6$, $AA_7$, $AA_8$, $AA_9$, $AA_{10}$, $AA_{11}$, $AA_{12}$, $AA_{13}$, $AA_{14}$, $AA_{15}$, $AA_{16}$, $AA_{18}$, $AA_{19}$, $AA_{20}$-COOH. The reference protein therefore has amino acids 1-20 in the N to C orientation. A non-limiting example of a permutation of this protein is: $NH_2$— . . . $AA_9$, $AA_{10}$, $AA_{11}$, $AA_{12}$, $AA_{13}$, $AA_{14}$ . . . $AA_2$, $AA_3$, $AA_4$, $AA_5$, $AA_6$, $AA_7$, $AA_8$ . . . —COOH, wherein the ellipses represent other amino acids that may or may not be part of a fusion protein that contains such permutated segments. Such fusion proteins are described further below.

Reference to N-terminal and C-terminal when referring to amino acids within a polypeptide is used herein as a convenience to describe orientation, but does not necessarily mandate that the particular amino acid be at the N- or C-terminal amino end of the polypeptide itself.

In embodiments the disclosure comprises segments of an RBP protein, wherein the segments comprise an amino acid sequence that is 90, 91, 92, 93, 94, 95, 96, 97, 98 or 99% or completely identical to the sequence (the tteRBP, described further below):

```
                                              (SEQ ID NO: 1)
KEGKTIGLVISTLNNPFFVTLKNGAEEKAKELGYKIIVEDSQNDSSK

ELSNVEDLIQQKVDVLLINPVDSDAVVTAIKEANSKNIPVITIDRSA

NGGDVVSHIASDNVKGGEMAAEFIAKALKGKGNVVELEGIPGASAAR

DRGKGFDEAIAKYPDIKIVAKQAADFDRSKGLSVMENILQAQPKIDA

VFAQNDEMALGAIKAIEAANRQGIIVVGFDGTEDALKAIKEGKMAAT

IAQQPALMGSLGVEMADKYLKGEKIPNFIPAELKLITKENVQ.
```

The tteRBP sequence that includes and counts the terminal Met in amino acid numbering is SEQ ID NO:2.

Variants of the RBP and MBP or target protein bearing one or several amino acid substitutions or deletions are also included in this disclosure. In embodiments, the variants comprise mutations, including but not necessarily limited to conservative amino acid substitutions, and mutations that enhance one or more properties of the RBP or the MBP. In embodiments, a sequence having at least 90% similarity to any sequence described herein can be shorter or longer than the described sequence. The skilled artisan can easily assess whether such variants are appropriate for a method of this disclosure.

The location of the N-terminal and C-terminal amino acid(s) where an RBP or MBP according to this disclosure can be separated into segments is referred to as a permutation site, and may be referred to as a circular permutation site. All individual permutation sites, all combinations of permutation sites, and all protein segments delineated by each single and every combination of permutation sites is encompassed by this disclosure.

In embodiments, the disclosure includes a fusion protein comprising first and second segments of the RBP wherein the second segment is located N-terminal to the first segment relative to an intact wild type amino acid sequence of an RBP. In embodiments, the fusion protein comprises the amino acid sequence of the first segment and the amino acid sequence of the second segment together comprise an amino acid sequence that has at least 90% identity with a segment of SEQ ID NO:1 that is at least 251 amino acids in length, and wherein the amino acid sequences of the first and second segments do not overlap with each other. In embodiments, the first segment has as its first amino acid position 34, 60, 70, 85, 97, 125, 136, 186 or 210 of SEQ ID NO:1. The first segment can optionally extended by any number of amino acids up to amino acid number 277 of SEQ ID NO:1. Thus, in one embodiment, the first segment ends at amino acid 277 of SEQ ID NO:1. In embodiments, the first segment has at least 90% identity with a segment of SEQ ID NO:1 that is amino acids 34-254 of SEQ ID NO:1, 60-254 of SEQ ID NO:1, 70-254 of SEQ ID NO:1, 85-254 of SEQ ID NO:1, 97-254 of SEQ ID NO:1, 125-254 of SEQ ID NO:1, 136-254 of SEQ ID NO:1, 186-254 of SEQ ID NO:1, or 210-254 of SEQ ID NO:1. In embodiments, the first segment has at least 90% identity with a segment of SEQ ID NO:1 that begins with one of amino acids 34 of SEQ ID NO:1, 60 of SEQ ID NO:1, 70 of SEQ ID NO:1, 85 of SEQ ID NO:1, 97 of SEQ ID NO:1, 125 of SEQ ID NO:1, 136 of SEQ ID NO:1, 186 of SEQ ID NO:1, or 210 of SEQ ID NO:1 and ends with an amino acid from 254 of SEQ ID NO:1 to 277 of SEQ ID NO:1.

In embodiments, the second segment comprises a contiguous amino acid sequence of SEQ ID NO:1 that begins with amino acid number 1, 2, 3, or 4 of SEQ ID NO:1 and ends with amino acid number 33, 59, 69, 84, 96, 124, 135, 185, or 209 of SEQ ID NO:1. In embodiments, the second segment ends at amino acid 96 or amino acid 124 of SEQ ID NO:1. In embodiments, the second segment has at least 90% identity with a segment of SEQ ID NO:1 that begins with amino acid number 1, 2, 3, or 4 of SEQ ID NO:1 and ends with amino acid number 33, 59, 69, 84, 96, 124, 135, 185, or 209 of SEQ ID NO:1.

The term "fusion" and "fuse" as used herein mean a protein that contains amino acid segments from distinct sources, wherein the proteins are made using recombinant molecular biology approaches that adapt standard approaches that are known in the art. It is not intended to mean chemical formation of polypeptides, such as by non-protein translation approaches, such as solid or solution phase based peptide synthesis approaches. Likewise, the fusion proteins are not made by chemical conjugation of pre-existing peptides in the absence of translation.

As described above, in certain approaches a segment from a C-terminal region of the wild type protein is moved to a position that is N-terminal to said wild type C-terminal region, and vice versa. But in alternative embodiments the wild type orientation can be maintained, provided first and second segments are included and are separated from one another, as described further herein. In embodiments, a fusion protein described herein does not contain only one RBP or MBP segment, i.e., the fusion proteins comprises more than one RBP or MBP segment which are separated from each other by intervening amino acids that are not RBP or MBP amino acids, such as linkers and target proteins described further below. Without intending to be bound by any particular feature, it is consider that this disclosure comprises improvements in increasing protein expression and/or solubility that are distinct from certain other approaches, such as those described in PCT/US16/56832, published as WO 2017/066441.

In more detail, in one non-limiting and representative approach, the present disclosure presents a novel approach to incorporating an expression tag into a fusion protein. In one approach the disclosure provides a circular permutant. In embodiments circular permutants are used in a novel purification system which utilizes split Histidine (His) tags fused to each of the N- and C-termini of the fusion protein, which is referred to in some embodiments as a split His tag. The present system is applicable to any expression tag, including but not limited to RBP and MBP.

In certain embodiments, fusion proteins produced according to the methods of this disclosure have improved and/or different characteristics that relate at least in part to the discontinuous inclusion of two segments of the RBP or the MBP in the fusion protein. In non-limiting examples, such improvements can be detected by comparison to a suitable reference (i.e., a control or control value). In embodiments, the reference is a value based on one or more properties of a fusion protein that comprises only one segment of the RBP or the MBP and a target protein. In embodiments, the reference can include a standardized value or curve(s), and/or experimentally designed controls such as a known or determined expression value for a protein, such as a target protein, wherein the expression is measured for the target protein without it being in a fusion protein that contains two discontinuous segments of the RBP or the MBP. A reference value may also be depicted as an area on a graph, or a value obtained from an elution profile, or a solubility value, or a protein degradation value, and/or the total amount of protein that is expressed and/or recovered from an expression system, such values being determined based on any suitable parameter, such as the mass, moles, etc. of the protein that is produced and/or separated from the expression system. In non-limiting embodiments fusion proteins can be evaluated using any suitable approaches, which include but are not limited to Western blotting, spectroscopy (such as circular dichroism, fluorescence, absorbance, NMR), circular dichroism, mass spectrometry, Gel electrophoresis under denaturing conditions, gel electrophoresis under non-denaturing conditions, 2D gel electrophoresis, chromatography, including but not limited to cation-exchange chromatography, high-performance liquid chromatography (HPLC), chromatography-mass spectroscopy (LC/MS), immunological methods, and analysis of resistance to degradation using a variety of approaches known to those skilled in the art. In embodiments, the fusion proteins can be evaluated based on actual or predicted ability to bind to sugar, i.e., ribose for RBP and maltose for MBP.

In embodiments, the disclosure relates to fusion proteins that comprise RBP segments or derivatives thereof such that they retain sufficient homology to WT RBP (such as RBP expressed by *Thermoanaerobacter tengcongensis* (tteRBP, described further below) that when they fold together (i.e., a tertiary structure is formed) a functional ribose binding pocket is preserved. The structure of RBP, and its residues that contribute to ribose binding, are known in the art. (See, for example, "The backbone structure of the thermophilic *Thermoanaerobacter tengcongensis* ribose binding protein is essentially identical to its mesophilic *E. coli* homolog." BMC Structural Biology (2008) 8:20; and Analysis of ligand binding to a ribose biosensor using site-directed mutagenesis and fluorescence spectroscopy. Protein Science (2007) 16, 362-368, the descriptions of each of which are incorporated herein by reference). In embodiments, a fusion protein of this disclosure binds more ribose relative to a fusion protein that comprises only one RBP segment. In embodiments, a fusion protein of this disclosure that is, for example, bound to a metal due to the inclusion of one or more His tags is in a non-covalent association with one or more ribose molecules. In embodiments, a fusion protein that is separated from a binding partner such as a suitable metal is in a non-covalent association with one or more ribose molecules. In embodiments, a fusion protein of this disclosure that is in a non-covalent complex with ribose molecules is more stable and/or is more soluble than a fusion protein that contains only one RBP segment. In an embodiment ribose is added to, for example, a cell lysate prior to or during a fusion protein separation/isolation process. In embodiments, ribose is added to a cell culture medium in which a fusion protein of this disclosure is being expressed. In certain embodiments, an fusion protein comprising two RBP segments includes one or more of *E. coli* RBP amino acids S9, N13, F15, F16, N64, D89, S103, 1132, F164, N190, F214, D215 and Q235, or the *T. tengcongensis* RBP amino acids that are the equivalents thereof. In embodiments, an RBP segment of this disclosure binds specifically to D-ribose. In embodiments, the amino acid sequence of an RBP protein of this disclosure comprises or consists of SEQ ID NO:1, which is RBP produced by *T. tengcongensis*. The amino acid residues of this amino acid sequence can be compared by those skilled in the art to the RBP sequence of RBP produced by *E. coli*, which is known in the art and can be found, for example, under GenBank accession number SMH27141.1, the amino acid sequence from which is incorporated herein by reference as of the filing date of this application or patent. In this regard, the ribose binding residues of RBP produced by *E. coli* that are involved in the ribose binding pocket comprise S9, N13, F15, F16, N64, D89, S103, 1132, F164, N190, F214, D215 and Q235, and the homologous amino acids in tteRBP can be readily recognized by comparison to the *E. coli* sequence.

With respect to ribose binding, in a specific and non-limiting example, amino acids 17 and 18 and 217 and 218 of SEQ ID NO:1 and a number of amino acids between 18 and 217 are considered to be necessary for RBP to bind to ribose. Because the two segments in the present invention together include the amino acids of SEQ ID NO:1 numbered 4 to 254, which includes the aforementioned amino acid residues (in contrast to the linear RBP in described in WO 2017/066441) and because the two segments are capable of interacting with each other and adopting a suitable tertiary structure for ribose binding (unlike the segments described in the published PCT application WO 2013/101915), absent certain modifications to the sequence of the two segments, the RBP formed when the two segments fold together will be capable of binding ribose. However, it should be understood that ribose binding is not required for the two segments of RBP to fold together properly. In this regard, it has been demonstrated by the inventors that the residues 17+18, and residues 217+218 can be been modified in RBP creating mutants which cannot bind ribose but are still folded and remain stable. It is expected that this approach will apply to the folding of two segments wherein one or more of the residues 17, 18, 217 and 218 have been similarly mutated (i.e., they will still be able to fold together properly and be stable). Thus, the disclosure includes such mutated proteins. In one embodiment, the disclosure includes a mutation that is a Cys to Ser alteration relative to a native sequence RBP sequence, such as a Cys to Ser alteration at position 101 in SEQ ID NO:1 (position 102 in SEQ ID NO:2).

Gene and Protein Structures

FIG. 1 compares one embodiment of this disclosure (FIG. 1, panel B) with a linear tag, such as that described in PCT/US16/56832 published as WO 2017/066441. (FIG. 1, panel A). In the linear tag, the target protein gene is appended to either the 3'-end of the RBP gene (shown as top linear RBP tag in FIG. 1A) or the 5'-end of the RBP gene (shown as bottom linear RBP tag in FIG. 1A). The RBP gene encodes for full-length RBP (amino acids [AA] 1-277, in normal, sequential order, or at a minimum, encodes the RBP amino acids 34 [Gly] to 210 [Gln]). RBP and the target protein are separated by a peptide linker (labeled 'link' in FIG. 1) and a protease cleavage site (labeled 'cleave' in FIG. 1), to enable recovery of the untagged target protein. A nucleotide sequence encoding for a full histidine tag (typically 6-8 His residues) is placed at the beginning or end of the gene to facilitate purification.

In contrast, in the split, circularly-permuted tag of this disclosure (using RBP as a representative solubility tag), the target protein gene is inserted internally into the RBP gene (FIG. 1B), and thus can be used to produce a fusion protein encoded by the gene with the same protein orientation. In addition, the RBP gene can be rearranged such that it encodes for an RBP protein that is permuted.

The disclosure includes variations of amino acid positions that are expressly described herein, so long as the fusion protein includes properties that are improved relative to a reference.

In one embodiment the RBP gene is rearranged such that it encodes for an RBP protein that is circularly permuted at amino acid position 97. The amino acid sequence of permuted RBP in certain embodiments begins with amino acid 97 (numbered according to the wild-type RBP sequence), continues through amino acid 277, through a linker sequence of variable composition (the target protein can be inserted here), to amino acid number 1, and ends with amino acid 96. The target protein gene is flanked by two nucleotide sequences that each encode for peptide linkers and a protease cleavage site, to facilitate recovery of the untagged target protein. A sequence encoding a split-His tag can be placed at each end (i.e., C- and N-termini) of the final gene. The design and rationale for an embodiment of the split-His tag is described below. Representative fusion proteins expressed by the genes in FIG. 1 are shown schematically in FIG. 2. In an embodiment, the 97-277 segment can be C-terminal to the RBP 1-96 segment. An optional linker can be inserted between the split-His tag and the adjacent segment of RBP.

For E. coli protein expression systems, a methionine will generally be added to the N-terminus of the fusion protein. In the split, circularly permuted tags described here, the methionine precedes the first split His tag or, if a split His tag is not in use, the first segment of RBP or MBP. In some embodiments, the N-terminal methionine is not counted in the amino acid numbering of the protein (SEQ ID NO:1 does not include the first Met). Some of the DNA sequences given herein for expression of proteins include a stop codon at the 3' end. A plasmid containing the DNA sequence does not need to include that stop codon.

Internal Fusion Vs. End-to-End Fusion

Figure 3:
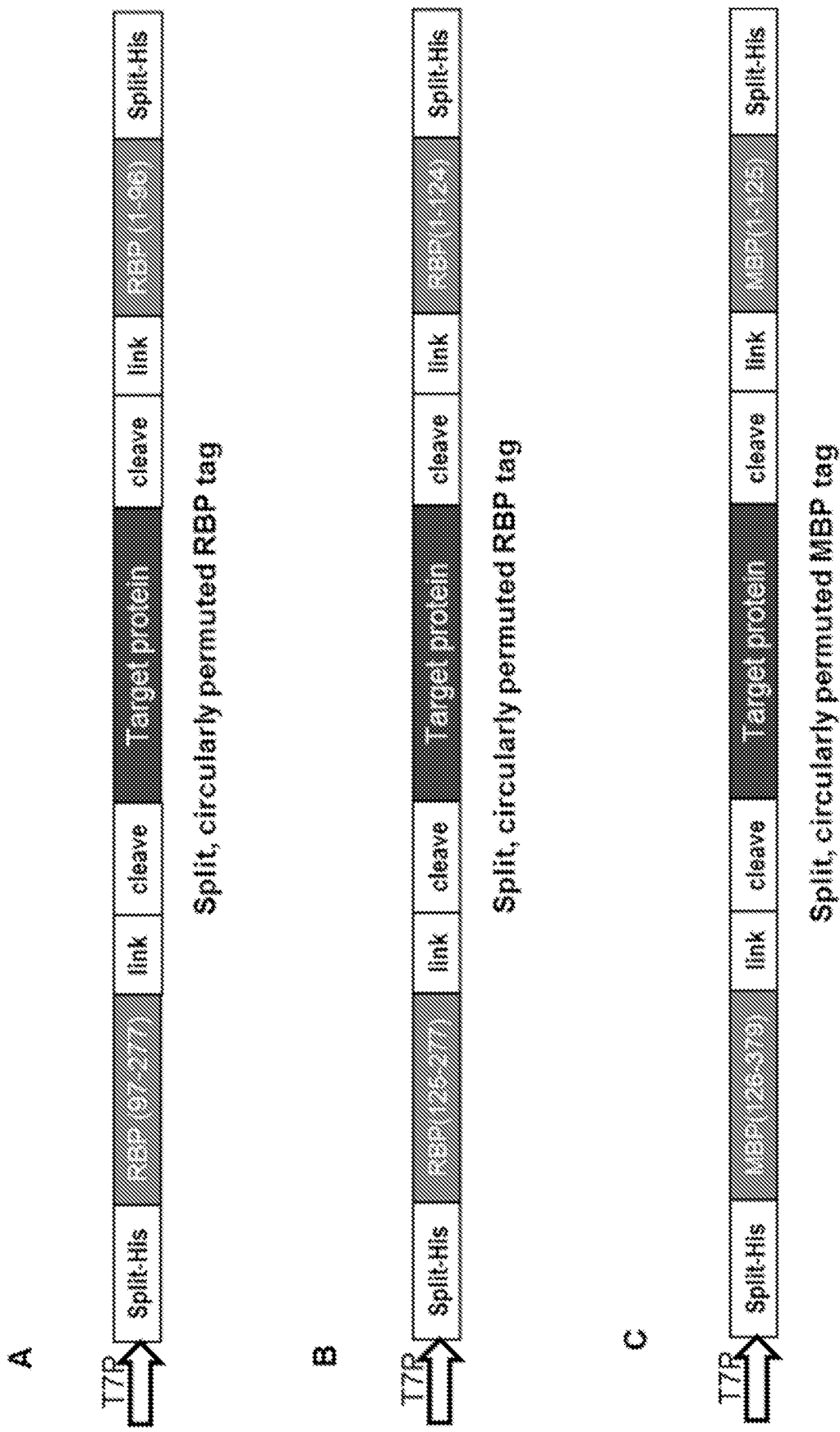
FIG. 3, panels A, B and C provide schematic comparisons of different first and second segments of RBP in illustrative split, circularly permutated fusion proteins of this disclosure.

In the disclosure, the target protein is inserted internally into RBP (FIGS. 1B and 2B), whereas the linear system of the 832 PCT application published as WO 2017066441 places the two proteins end-to-end (FIGS. 1A and 2A). In the current system, and without intending to be constrained by any particular theory, it is considered that the RBP folds by docking of the 1-96 and 97-277 fragments, which extend from both termini of the target protein. This effectively yields a closed, topologically circular protein in which the target protein is protected from exoprotease attack at both its N- and C-termini by the presence of the extremely stable RBP protein (FIG. 3A). Likewise if the RBP tag is circularly permuted at AA 125, the RBP folds by docking of the 1-124 and 125-277 fragments, which extend from both termini of the target protein.

Circular Permutation Vs. Normal Amino Acid Sequence of RBP

The same benefits of internal fusion could be achieved by inserting the target protein into position 97 of the normal RBP sequence, i.e. (RBP 1-96)-(target protein)-(RBP 97-277) (FIG. 2C), instead of the permuted RBP sequence, i.e. (RBP 97-277)-(target protein)-(RBP 1-96)(or into position 125 of the normal RBP sequence). In the former, the target protein is still protected from exoprotease degradation by the RBP protein at both its N- and C-termini. The circular permutation is employed in order to make a unique, high-affinity binding site (split-His tag) that will allow us to specifically purify the full-length protein, and reject those that are truncated either by protease cleavage or by incomplete translation. Although embodiments excluding amino acids 1-33 and/or amino acids 211-277 will dock properly, they will be unable to bind ribose, and as a result will likely be less stable than embodiments containing both these segments In various embodiments, one segment of a fusion protein comprises amino acids 34-96 of the RBP, while another segment comprises amino acids 97-211. In various embodiments, one segment of a fusion protein of this comprises amino acids 34-124 of the RBP, while another segment comprises amino acids 125-211. These variations can be made in the context of the split permuted RBP: wherein the "RBP (97-277)" segment is engineered to comprise or consist of RBP amino acids 97-211, and/or wherein the "RBP (1-96)" is engineered to comprise or consist of RBP amino acids 34-96, or wherein the "RBP (125-277)" segment is engineered to comprise or consist of RBP amino acids 125-211, and/or wherein the "RBP (1-124)" is engineered to comprise or consist of RBP amino acids 34-124. One of the two segments may be engineered to begin with any amino acids between 1 and 33 inclusive and end at the permutation site, and the other of the two segments may be engineered to start after the permutation site and end at any AA between 210 and 277 inclusive.

Other expression tags, such as MBP (e.g., pfu MBP) and GST, can be circularly permuted for the purposes of protein expression, including for enabling the effective use of split His tags. In one embodiment the MBP gene is rearranged such that it encodes for an MBP protein that is circularly permuted at amino acid position 126 (FIG. 3C). The amino acid sequence of permuted MBP in certain embodiments begins with amino acid 126 (numbered according to the wild-type MBP sequence), continues through amino acid 379, through a linker sequence of variable composition (the target protein can be inserted here), to amino acid number 1, and ends with amino acid 125. The target protein gene is flanked by two nucleotide sequences that each encode for peptide linkers and a protease cleavage site, to facilitate recovery of the untagged target protein. A split-His tag is placed at each end (i.e., C- and N-termini) of the final gene. In an embodiment, the N-terminus of the 1-125 segment of the MBP is truncated by one or more amino acids, such as, for example by 1, 2, 3, 4, etc. up to about 34 AAs, while the C-terminus of the 126-379 segment of the MBP is truncated by one or more amino acids, such as, for example by 1, 2, 3, 4, etc. up to about 60 AAs. These variations can be made in the context of the split permuted MBP.

Circular permutes of many proteins are less stable than the non-permuted protein. Circular permutes of some proteins from thermophilic organisms, however, such as tte-RBP (from *Thermoanaerobacter tengcongensis*) and PfuMBP (from *Pyrococcus furiosus*), are very stable.

Split His-Tag Vs. His-Tag

In embodiments of this disclosure, a "Split-His tag" means a His-tag that is divided between the N- and C-termini of the fusion protein. In certain embodiments, each of the two portions of the split His-tag comprises an adequate length of Histidines such that when the two portions are adjacent to one another recovery of the fusion protein is greater than a suitable control. In an embodiment, each split-His tag comprises a length of Histidines that is too short for stable binding to nickel ions that have been attached to beads.

In more detail, a His-tag is a linear sequence of n histidine residues where n is typically 6-8. His-tags achieve purification by binding specifically to nickel or cobalt ions that have been attached to beads. In all His-tag purification systems described to date, the His-tag placed at the N-terminus of the protein, at the C-terminus of the protein, or occasionally in the middle. The current system employs two split-His that are arrayed in close proximity and in approximately parallel orientation, by virtue of the structure of circularly permuted RBP. The distinction between split-His tag and conventional His-tag is that the two split-His tags must be very close to each other, such that the two tags can cooperatively bind the same, or nearby (on a molecular scale), nickel ion(s). Because the two split-His tags cooperatively bind, they act almost as a single His tag with a number of His equal to the sum of the number of His in the two split-His tags. For example, if each split His tag contains three His residues, their cooperative binding strength is close to or equal to that of a single His tag with six residues. To our knowledge, no expression system exists that has this feature. Further, engineering a split His tag into any recombinant protein, regardless of whether or not the other elements of the fusion proteins of this disclosure are included in the protein, is encompassed by this invention. Note that if one His-tag is placed at each terminus of the linear RBP-target protein fusion (FIG. 2), the two His-tags will not by physically close to each other and will therefore not bind cooperatively.

When a protein is circularly permuted, two sequential amino acids of the parent protein (typically in a surface loop) become the new amino and carboxy termini of the permuted protein. Therefore, the termini of a permuted protein are always close in space. If one attaches a split-His tag to each terminus, these tags are expected to project outward in roughly parallel orientation and be very close to each other (FIG. 2B). This tandem arrangement of 2× split-His binds nickel more tightly than a single His tag of the same number of His residues as each split His tag. What this means is that the full-length protein binds more tightly to nickel beads (or other appropriate stationary phase) than truncated proteins (which will contain only one or neither of the split-His tags). The full-length protein can then be selectively purified from fragments by a gradient of eluent (e.g. imidazole), represented in FIGS. 4 and 5.

Split His tags of equal length tend to work optimally for purification because both split His tags have an equal affinity to the nickel substrate of the column and as a result will release from the substrate under the same conditions and at the same time. In one embodiment, each split-His tag contains two, three, four, five, six, seven or eight His residues. In one embodiment, each split-His tag contains 2 to 20 His residues. The present disclosure, however, does not preclude split His tags of unequal length, such as one split-His tag containing two residues and the other containing three residues, or one split-His tag containing three His residues and the other split-His tag containing five, etc., as performed for FIG. 5. An optional linker can be inserted between the split-His tag and the adjacent segment of RBP.

Native proteins that are expressed by the cell being used for protein production may be rich in His and may therefore bind naturally to the nickel (or other suitable metal, such as cobalt) substrate. In order to make it easier to separate these proteins from the fusion protein, the disclosure includes use of split His tags that contain a total of more than six His residues. For example, the disclosure includes use two six or two eight residue split His tag, one on each end of the fusion protein. In such embodiments, a higher concentration of, for example, imidazole can be used to elute the native, His-rich proteins that have bound opportunistically to the nickel column than can be used when split His tags with fewer His residues are used.

Figure 12:
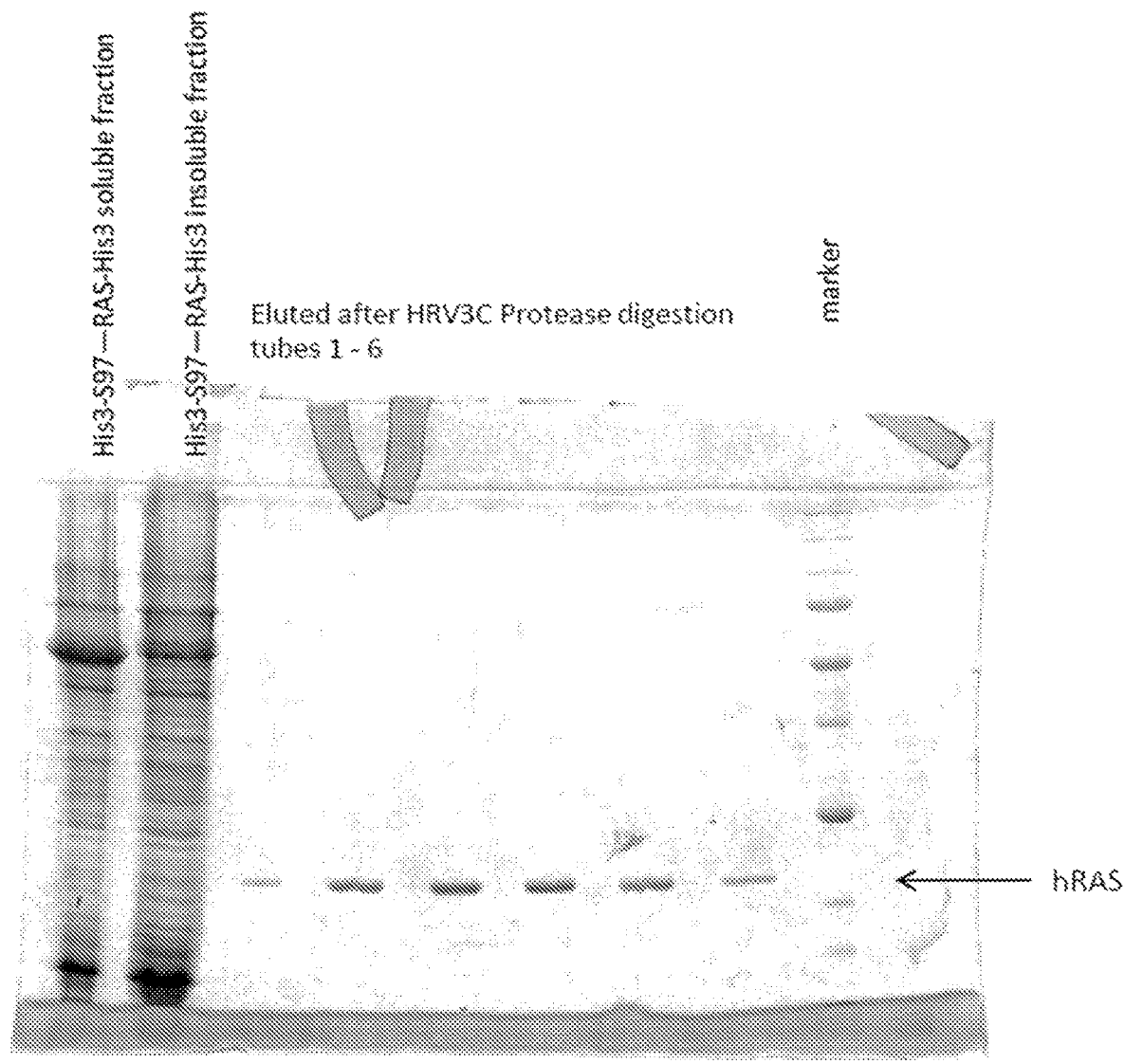
FIG. 12 provides a photographic representation of SDS-PAGE gel stained with Coomassie dye demonstrating that human hRAS is purified using just Nickel-NTA resin. Soluble fraction containing $His_3$-597-hRAS-$His_3$ protein was loaded on the column and hRAS was eluted after on-column protease digestion.
Figure 13:
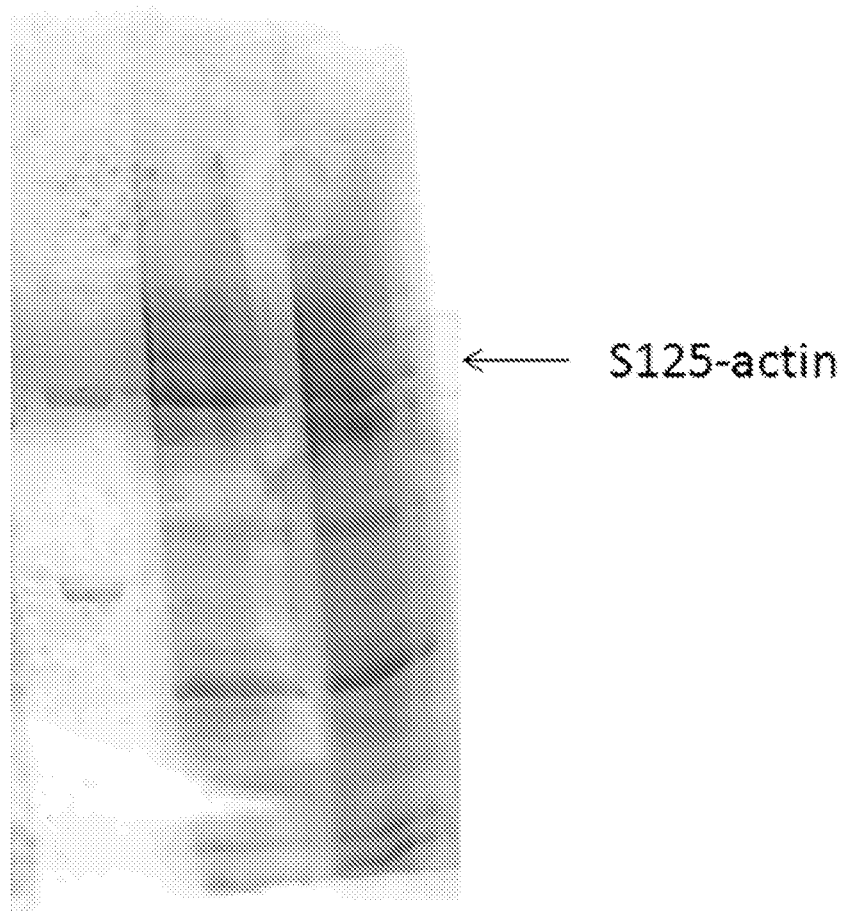
FIG. 13 provides a photographic representation of SDS-PAGE gel stained with Coomassie dye demonstrating high expression of yeast actin using split s125 tteRBP system.
Figure 14:
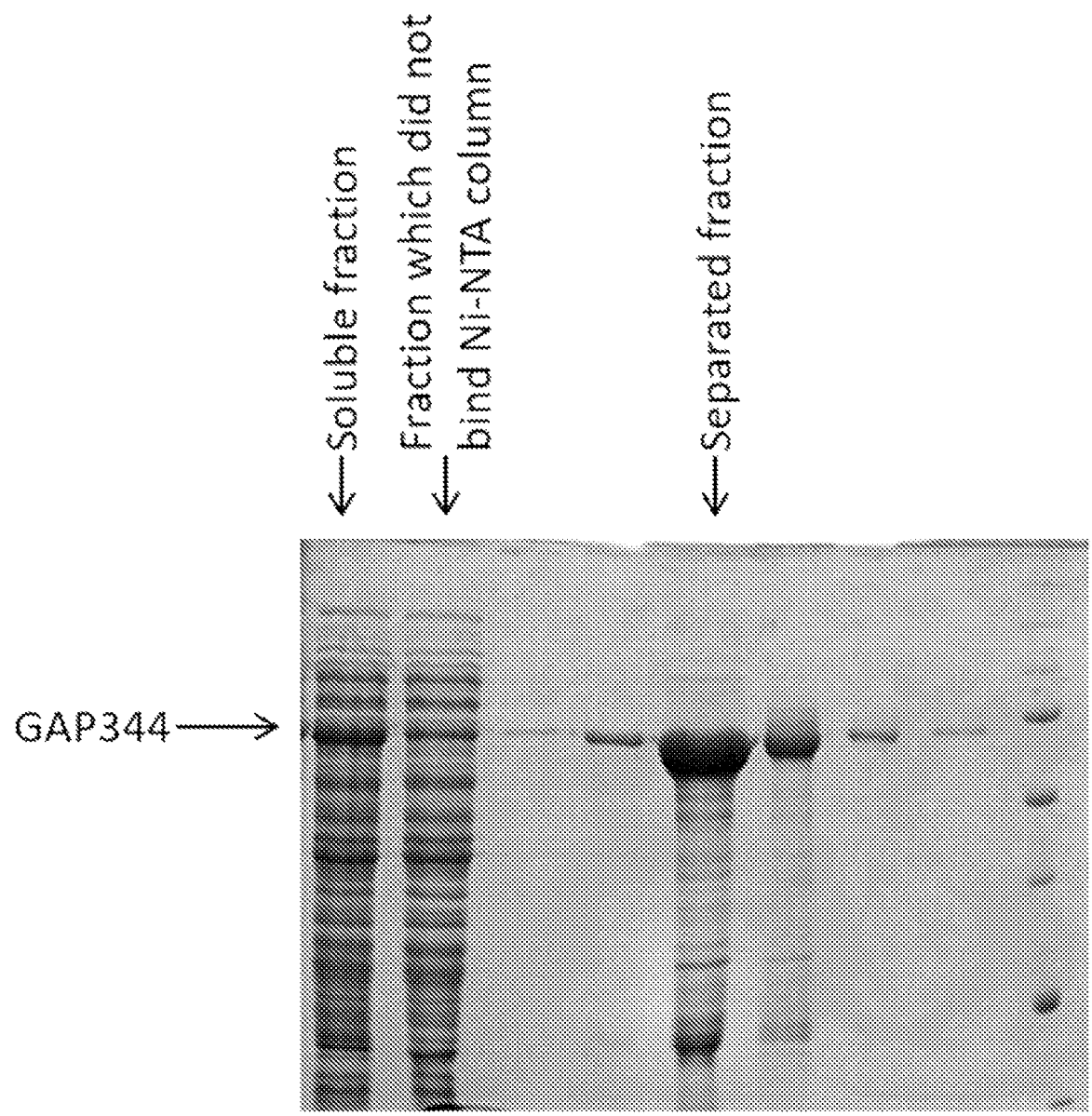
FIG. 14 provides a photographic representation of SDS-PAGE gel stained with Coomassie dye demonstrating high expression of human GAP344 using split s97 tteRBP system and subsequent purification on Nickel-NTA resin. GAP is GTPase-activating protein.

One advantage of the split-His tag circularly permuted RBP-target fusion protein production system is that single column purification is possible. (See, for example, representative and non-limiting embodiments described below under "One column purification of the target protein" and data shown represented by FIG. 12). Truncated fusion proteins will only have a single split His tag and will therefore only bind loosely to the nickel column's beads. These truncated fusion proteins and any His-rich native proteins can be eluted away using an eluent gradient. After eluting away the undesired fusion protein fragments, an appropriate protease can be run through the column to cleave the target protein from the RBP tags and release it from the column and into the mobile phase (e.g., buffer). If the protease contains a His tag of an appropriate length (e.g., six), it will bind to the column, either on the first pass or on a subsequent pass of the mobile phase through the column, thereby separating it from the released target protein. In some cases, the target protein may be nicked by proteases in the cell used for expressing the fusion protein. In that case there may be full-length target protein mixed with fragments of the target protein. Additional steps, using any of the techniques known to those skilled in chromatography and/or filtration, may be necessary to separate the fragments from the full-length target protein. For Instance, the heparin resin can be used to purify P53 further. Ion exchange, size exclusion, or affinity chromatography can also be used for purification, depending on the protein one wants to purify. The foregoing is applicable to a split-His tag circularly permuted RBP-target fusion protein production system. In certain embodiments of the disclosure as illustrated by the Figures, we used affinity chromatography using heparin resin to purify P53 and the size exclusion chromatography to purify MDM2 and Lect2 protein.

Circular Permutation at Other Positions (FIG. 10)

A circular permutant can be created by permuting the amino acid sequence at any position, although it is preferable to permutate surface loops to avoid perturbing protein structure. RBP has many surface loops (15) from which to choose when making a circular permutant. An aspect of this disclosure is our discovery that positions 97 and 124 are considered to be preferable sites to permute RBP due to their ability to yield a combination of stability, solubility, and foldability in the permutated proteins. Using a screening method that we developed [Ha et al. (2015), Chemistry & Biology 22, 1384] we discovered that position 97 is a favorable position to break the RBP sequence. It is possible to create similar constructs as that shown in FIG. 1 by permuting RBP at the other sites described in the above study, and this invention covers those designs as well. Other permutation sites on RBP include 34 (i.e., between AAs 33 and 34), 60, 125, 137, 186, and 210. The permutation can be within several AAs to either side of the aforementioned sites, as long as it is within the surface loops that comprise those sites (e.g., it can be at AA 121, 122, 123, 124, 126, 127, 128, 129, or 130 instead of at 125 in RBP). In embodiments where there is no permutation of RBP, the target protein and flanking nucleotides are inserted into the RBP at the aforementioned sites, or at another suitable site within the RBP. The same applies to MBP, which can be permuted at any of its loops, such as at 55, 82, 126, and 204.

Split His tags are to be employed with a circularly permuted tag, is the proximity and relative orientation of the N-terminus of the leading segment (e.g., the 125-277 segment of RBP) and the C-terminus of the trailing segment (e.g., the 1-124 segment of RBP) after the two segments fold together. If the N- and C-termini are oriented roughly parallel and are adjacent to each other, the split His tags will be roughly parallel and adjacent to each other and will generally work well. If the N- and C-termini are neither, the split His tags may not function optimally or at all. Thus, the disclosure provides modifying properties of the proteins using suitable length linkers, as described elsewhere herein.

Monomer Vs. Domain-Swapped Oligomer

In certain examples in which we inserted "lever" proteins into surface loops of "assembler" proteins (including RBP) we developed a technology by which such insertions would cause RBP to form domain-swapped dimers and oligomers (described in U.S. patent application Ser. No. 14/369,408; "the 408 application" published as WO/2013/101915). A purpose of this technology was to create self-assembling, domain-swapped biomaterials. This employed very short linkers (0-3 amino acids in length) to fuse lever proteins (with unusually long amino-to-carboxy terminal distances) into internal positions of assembler proteins. The lever protein then tears the assembler protein in two and holds the pieces so far apart that they cannot refold with each other within the same molecule. They are forced to refold with other molecules (domain swap).

In contrast to the '408 application, in the present invention, longer linkers are used (i.e., 15-30 amino acids, or longer, which can include the protease cleavage site if present) to join the target protein to the RBP segments. This allows RBP to accommodate target proteins with even the longest amino-to-carboxy distances without domain swapping (FIG. 2). In this regard, and without intending to be bound by any particular theory, the disclosure includes fusion proteins that are designed to be monomeric to achieve the benefits of split-His tag technology. In particular, the linkers and cleavage site are flexible enough and long enough to allow the two, separated and permuted sections of RBP become adjacent each other and fold to form a permuted and non-permuted RBP. In an embodiment, the linkers that flank the RBP, including both peptide linkers and protease cleavage (or the nucleotides coding therefore), are greater than the longest amino-to-carboxy dimension within the target protein. In an embodiment, the linkers that flank the RBP, including both peptide linkers and protease cleavage (or the nucleotides coding therefore), can be 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50 or more amino acids in length.

In more detail, with respect to the linkers that can be used with embodiments of this disclosure, it is preferable for the linkers to be flexible. In certain approaches, appropriate linkers are rich in small or polar amino acids such as Gly and Ser to provide suitable flexibility. Thus, the amino acid composition of the linkers is not particularly limited. Certain exemplary linker sequences are provided in the amino acid sequences and figures of this disclosure, which are not intended to limit the amino acid composition of the linkers. Further, approaches to design of flexible linkers are known in the art. (See, for example, Klein, et al. "Design and Characterization of Structured Protein Linkers with Differing Flexibilities." Protein Engineering, Design and Selection 27.10 (2014): 325-330, the disclosure of which is incorporated herein by reference).

In embodiments, the combination of the two linkers collectively include at least 30 amino acids, and thus are substantially longer than previous linkers that have been described with fusion proteins that include segments of RBP. In certain embodiments, the disclosure relates to configurations of a fusion protein wherein the two discontinuous RBP segments are be able to fold together (i.e., adopt a suitable tertiary structure such that the ribose binding pocket remains functional). In embodiments, linker sequences can comprise protease recognitions sites as described elsewhere herein. Without intending to be constrained to any particular theory, it is considered that the total number of amino acids in the linkers (and any protease sites if included) is approximately 30 amino acids in total when the end of the segment of RBP corresponding to the C terminus segment (such as of SEQ IN NO:1) is spatially proximal to amino acid 277 of SEQ ID NO:1. The 30 amino acids can be distributed between the linkers in any way, with the first and second linkers (plus protease sites if included) being between 0 and 30 amino acids long, again provided that the total is at least about 30 amino acids. In certain approaches it is preferable that there be at least a short (about 3, 4, 5, 10) linker between each termini of the target protein. In embodiments, the linkers and any protease sites if present together are about 20 amino acids longer than 30 if the segment of RBP corresponding to the C terminus segment of SEQ IN NO:1 ends at or near amino acid 254 (about 20 amino acids longer). This is because, and again without intending to be constricted by theory, in a folded protein of SEQ ID NO:1 beginning at amino acid number 4 and ending at amino acid number 254, the N and C termini are farther away from each other than in a folded protein of SEQ ID NO:1 that begins at amino acid number 4 and ends at amino acid number 277.

In particular, the length of the linkers can be adapted to account for the length of the RBP or MBP protein segments that are included in the fusion protein/encoded by the expression vectors. As a non-limiting example, if in certain embodiments, the first and second RBP segments collectively include 277 RBP amino acids, such as those depicted in SEQ ID NO:1, it is considered that total 30 amino acids of linker length is considered adequate. If for example, RBP amino acids are not included, such as by omitting the last 23 amino acids (i.e., 255 to 277), then the linker can be extended to substitute for those amino acids. In a non-limiting approach if the final RBP amino acid in a segment of the fusion protein is 254, a linker can be extended by an additional 23 amino acids. Similar linker length modifications can be made if other RBP amino acids are omitted. The same approach applies to MBP as well.

In a further embodiment, the disclosure includes a recombinant DNA molecule, such as an expression vector, encoding a fusion protein, comprising operatively-linked at least one nucleotide sequence coding for a target polypeptide at least one nucleotide sequence coding for the RBP segments as described herein.

Polynucleotide sequences are operatively-linked when they are placed into a functional relationship with another polynucleotide sequence. For instance, a promoter is operatively-linked to a coding sequence if the promoter affects transcription or expression of the coding sequence. Generally, operatively-linked means that the linked sequences are contiguous and, where necessary to join two protein coding regions, both contiguous and in reading frame. However, it is well known that certain genetic elements, such as enhancers, may be operatively-linked even at a distance, i.e., even if not contiguous. Promoters of the present disclosure may be endogenous or heterologous to the host, and may be constitutive or inducible. The appropriate promoter and other necessary vector sequences are selected so as to be functional in the host. Examples of workable combinations of cell lines and expression vectors include but are not limited to those described Sambrook, J., et al., in "Molecular Cloning: A Laboratory Manual" (1989, 4th edition: 2012)-, Eds. J. Sambrook, E. F. Fritsch and T. Maniatis, Cold Spring Harbor Laboratory Press, Cold Spring Harbor, or Ausubel, F., et al., in "Current Protocols in Molecular Biology" (1987 and periodic updates), Eds. F. Ausubel, R. Brent and K. R. E., Wiley & Sons Verlag, New York; and Metzger, D., et al., Nature 334 (1988) 31-6. Many useful vectors for expression in bacteria, yeast, mammalian, insect, plant or other cells are known in the art and may be obtained from vendors including, but not limited to, Stratagene, New England Biolabs, Promega Biotech, and others. In addition, the construct may be joined to an amplifiable gene so that multiple copies of the gene may be obtained. Thus, and without intending to be constrained by any particular theory, it is considered that one of the advantages of using highly soluble proteins such as RBP and MBP as overexpression tags as described herein is that they are so soluble that a stronger expression promoter, such as the T7 promoter (T7P in FIG. 1), can be used to drive protein production to very high levels. We have discovered that the presently described approaches facilitate expression of so much of the RBP fusion protein (FIG. 1B) that any native *E. coli* proteins that are present are at very small concentrations, making purification easier. However, any other suitable promoters (ranging from strong to weak promoters) can be used in the expression vectors of this disclosure, some examples of which include but are not limited to promoters that are provided with commercially available expression vectors, such as the Pm/xylS promoter from Vectron Biosolutions. Other specific examples are known and are described in, for example, "A comparative analysis of the properties of regulated promoter systems commonly used for recombinant gene expression in *Escherichia coli*" Microbial Cell Factories, 201312:26, from which the disclosure of promoters is incorporate herein by reference. The promoters used in embodiments or the disclosure may be constitutive promoters, or they may be inducible.

Furthermore, the expression systems are not limited to prokaryotic systems, and thus may be configured for expression in eukaryotic systems, such as yeast, animal systems such as baculovirus-insect cell systems, mammalian cell expression systems, and cell free expression systems that are known in the art and that, when given the benefit of the present disclosure, can also be used. Suitable expression vectors are known in the art and can be adapted for use in methods of this disclosure.

Expression of the proteins can be also be scaled to produce any desired amount of the proteins, such as by batch scaling, and can be used to produce milligram, gram, or kilogram quantities of the proteins. Such quantities can refer to production of the fusion protein, or of the target protein if the target protein is separated from the fusion protein.

In more detail with respect to expression systems, DNA constructs prepared for introduction into a host typically comprise a replication system recognized by the host, including the intended DNA fragment encoding the desired target fusion peptide, and will can also include transcription and translational initiation regulatory sequences operatively-linked to the polypeptide encoding segment. Expression systems (expression vectors) may include, for example, an origin of replication or autonomously replicating sequence (ARS) and expression control sequences, a promoter, an enhancer and necessary processing information sites, such as ribosome-binding sites, RNA splice sites, polyadenylation sites, transcriptional terminator sequences, and mRNA stabilizing sequences.

Expression and cloning vectors can contain a selectable marker, a gene encoding a protein necessary for the survival or growth of a host cell transformed with the vector, although such a marker gene may be carried on another polynucleotide sequence co-introduced into the host cell. Only those host cells expressing the marker gene will survive and/or grow under selective conditions. Typical selection genes include but are not limited to those encoding proteins that (a) confer resistance to antibiotics or other toxic substances, e.g., ampicillin, tetracycline, etc.; (b) complement auxotrophic deficiencies; or (c) supply critical nutrients not available from complex media. The choice of the proper selectable marker will depend on the host cell, and appropriate markers for different hosts are known in the art.

The expression vectors containing the polynucleotides of interest can be introduced into the host cell by any method known in the art. These methods vary depending upon the type of cellular host, including but not limited to transfection employing calcium chloride, rubidium chloride, calcium phosphate, DEAE-dextran, other substances, and infection by viruses. Large quantities of the polynucleotides and polypeptides may be prepared by expressing the polynucleotides in compatible host cells. The most commonly used prokaryotic hosts are strains of *Escherichia coli*, although other prokaryotes, such as *Bacillus subtilis* may also be used.

Construction of a vector according to the present disclosure employs conventional ligation techniques. Isolated plasmids or DNA fragments are cleaved, tailored, and religated in the form desired to generate the plasmids required. If desired, analysis to confirm correct sequences in the constructed plasmids is performed in a known fashion. Suitable methods for constructions expression vectors, preparing in vitro transcripts, introducing DNA into host cells, and performing analyses for assessing expression and function are known to those skilled in the art.

The DNA construct comprise linker peptides as illustrated herein. As described above, the linkers and cleavage site are flexible enough and long enough to allow the two, separated and permuted sections of RBP become adjacent each other and fold to form a permuted RBP.

In cases where it is desired to release one or all of the solubility and expression tags out of a fusion protein, the linker peptide(s) can be constructed to comprise a proteolytic cleavage site. Thus, a recombinant DNA molecule, such as an expression vector, encoding a fusion protein comprising at least one polynucleotide sequence coding for a target polypeptide, a polynucleotide sequence coding for the RBP-solubility tags as described herein, and additionally comprising a nucleic acid sequence coding for a peptidic linker comprising a proteolytic cleavage site, represents a non-limiting embodiment of this invention. In certain embodiments, the expression vector comprises codons optimized for expression in the host cell.

As discussed above, fusion proteins of this disclosure may or may not contain protease recognition sites. If a protease recognition site is included it can be comprised within a linker sequence. Suitable protease recognition sites are known in the art and can be adapted with embodiments of this disclosure. In embodiments, the protease recognition site can comprise a site that is recognized by any of plant, viral, bacterial and/or animal proteases. Animal proteases include acid proteases secreted into the stomach (such as pepsin) and serine proteases present in duodenum (trypsin and chymotrypsin). Proteases present in blood serum (thrombin, plasmin, Hageman factor, etc.) recognize sites that can also be used. Other proteases are present in leukocytes (elastase, cathepsin G), and some venoms also contain proteases, such as pit viper haemotoxin; sites that are recognized by such proteases are included in the disclosure. It will also be recognized that amino acid sequences recognized by proteases expressed by bacteria in the gut of various animals, including humans, or by the animals themselves in various parts of their anatomy, such as their gut, digestive system or circulatory system, can also be incorporated into the fusion proteins. In such cases, the separation of the target protein from the fusion protein can occur in that part of the animal's anatomy. Thus, in embodiments, a target protein of this disclosure can comprise a protein-based pro-drug (or other biologically active protein) which is activated via liberation from the fusion protein only once it is administered to an animal that expresses the cognate protease. Protease recognition sites that can be used in this invention are known in the art. For example, see the table of protease recognition sites available at www.proteinsandproteomics.org/content/free/tables_1/table11.pdf, the disclosure of which is incorporated herein by reference.

In specific but non-limiting embodiments, protease cleavage sites that can be used in embodiments of this disclosure include Tobacco etch virus (ENLYFQ/G; SEQ ID NO:16, Enterokinase site (DDDDK/ SEQ ID NO:13), Factor Xa site IEGR/ (SEQ ID NO:14) and Thrombin (LVPR/GS SEQ ID NO:15).

Protease sequences (or other cleavage sites) that are not included in the target protein can be designed and included by analysis of the amino acid sequence of the target protein, thus avoiding or minimizing cleavage of the target protein. In embodiments, publicly available tools for protease sites can be used to determine protease cleavage sites, such as PeptideCutter (available at web.expasy.org/peptide_cutter/).

In other embodiments, the fusion proteins can comprise amino acid sequences that can be cleaved to, for example, liberate the target protein, but not necessarily by a protease, and thus may be cleaved non-enzymatically. Such sequences can be included in the linkers. In certain embodiments, such sequence can be, for example, particularly susceptible to acid hydrolysis, or by exposure to other chemicals, or by heat treatment. In certain approaches the fusion proteins comprise sequences that are designed to be exclusively or preferentially cleaved by cyanogen bromide, which cleaves peptide bonds after a methionine. Likewise, the fusion proteins may be designed to be exclusively or preferentially cleaved at tryptophanyl, aspartyl, cysteinyl, and/or asparaginyl peptide bonds. Acids such as trifluoroacetic acid and formic acid may also be used for such non-enzymatic proteolysis. Approaches such as these can be adapted to alter conditions in which a fusion protein of this disclosure is treated, such as by modifying pH, temperature, salt concentrations and the like so that preferential cleavage of the target protein can be achieved. Combinations of these cleavage mechanisms or approaches can be used in a single fusion protein, including incorporating different cleavage mechanisms between the target protein and each of the RBP segments or incorporating more than one cleavage mechanism between the target protein and one or both of the RBP segments.

The invention is demonstrated using several target proteins as described in the Examples. These include Leukocyte Cell Derived Chemotaxin 2 (LECT2), Human mouse double minute 2 homolog (MDM2) also known as E3 ubiquitin-protein ligase Mdm2, p53, hRAS, actin and GTPase-activating protein (GAP). Thus, the disclosure demonstrates embodiments with proteins of vastly different amino acids compositions, sizes and function. Accordingly, it is expected that the target protein that is included in the fusion proteins of this disclosure may be any polypeptide of interest. In embodiments, a target polypeptide according to the present disclosure may be any polypeptide required or desired in larger amounts and therefore may be difficult to isolate or purify from other sources. Non-limiting examples of target proteins that can produced by the present methods include mammalian gene products, such as enzymes, cytokines, growth factors, hormones, vaccines, antibodies and the like. In embodiments, overexpressed gene products of the present disclosure include gene products such as p53, erythropoietin, insulin, somatotropin, growth hormone releasing factor, platelet derived growth factor, epidermal growth factor, transforming growth factor a, transforming growth factor 13, epidermal growth factor, fibroblast growth factor, nerve growth factor, insulin-like growth factor I, insulin-like growth factor II, clotting Factor VIII, superoxide dismutase, α-interferon, γ-interferon, interleukin-1, interleukin-2, interleukin-3, interleukin-4, interleukin-5, interleukin-6, granulocyte colony stimulating factor, multi-lineage colony stimulating activity, granulocyte-macrophage stimulating factor, macrophage colony stimulating factor, T cell growth factor, lymphotoxin and the like. In embodiments overexpressed gene products are human gene products. The present methods can readily be adapted to enhance secretion of any overexpressed gene product which can be used as a vaccine. Overexpressed gene products which can be used as vaccines include any structural, membrane-associated, membrane-bound or secreted gene product of a mammalian pathogen. Mammalian pathogens include viruses, bacteria, single-celled or multi-celled parasites which can infect or attack a mammal. For example, viral vaccines can include vaccines against viruses such as human immunodeficiency virus (HIV), vaccinia, poliovirus, adenovirus, influenza, hepatitis A, hepatitis B, dengue virus, Japanese B encephalitis, Varicella zoster, cytomegalovirus, hepatitis A, rotavirus, as well as vaccines against viral diseases like measles, yellow fever, mumps, rabies, herpes, influenza, parainfluenza and the like.

Bacterial vaccines can include vaccines against bacteria such as *Vibrio cholerae, Salmonella typhi, Bordetella pertussis, Streptococcus pneumoniae, Hemophilus influenza, Clostridium tetani, Corynebacterium diphtheriae, Mycobacterium leprae, R. rickettsii, Shigella, Neisseria gonorrhoeae, Neisseria meningitidis, Coccidioides immitis, Borellia burgdorferi*, and the like. A target polypeptide may also comprise sequences; e.g., diagnostically relevant epitopes, from several different proteins constructed to be expressed as a single recombinant polypeptide.

In embodiments, the target protein can comprise a protein that can be suitable for use as a nutraceutical, a dietary or other food supplement, a food additive, a filler, a binder, or for any purpose related to human and non-human animal nutrition. In an embodiment, the target protein is intended for human consumption, or for veterinary purposes, including but not limited to the purposes of providing a feed, feedstock, a dietary supplement, or other food component to, for example, animals that are used in an agricultural industry, or for companion animals. In embodiments, the non-human animals are bovine animals, poultry, porcine animals, felines, canines, equine animals, or fish. In embodiments, the protein can be comprised within intact cells, such as in a cell culture, or in can be provided as a cell lysate. In embodiments, cells that produce the protein can be used as a probiotic agent, which could be for instance fed to a recipient, and/or could be used as an inoculant so that that the cells could colonize for example some or all of the gastrointestinal tract of the animal (or elsewhere) and provide an ongoing supply of the target protein, whether or not it remains as a component of the fusion protein. In embodiments, the protein comprises a high proportion of essential amino acids, i.e., an abundance of any one or combination of phenylalanine, valine, threonine, tryptophan, methionine, leucine, isoleucine, lysine, and histidine. In embodiments, the protein comprises an enzyme that is beneficial to a person who may produce an inadequate amount of the enzyme.

The recombinant proteins of the inventions can be recovered by conventional methods. Thus, where the host cell is bacterial, such as *E. coli* it may be lysed physically, chemically or enzymatically and the protein product isolated from the resulting lysate. It is then purified using conventional techniques, including but not necessarily limited to conventional protein isolation techniques such as selective precipitation, adsorption chromatography, and affinity chromatography, including but not limited to a monoclonal antibody affinity column.

Proteins of the present invention that are expressed with a histidine tail (HIS tag) as described above can easily be purified by affinity chromatography using an ion metal affinity chromatography column (IMAC) column. In embodiments where the permute or non-permute RBP formed when the two segments of the fusion protein fold together is capable of binding ribose, the fusion protein will bind to any ribose in the cells expressing it. In some cases, the amount of fusion protein will exceed the supply of ribose in the cell. To increase that supply and ensure that each fusion protein is bound to a ribose, ribose can be added to the media in which the cells expressing the fusion protein are growing. Alternatively, the ribose can be added after the cells are lysed. In either case, the additional ribose will ensure that all of the fusion protein is bound to a ribose.

When used as part of an expression construct designed for the expression of the coded protein in an appropriate host the disclosure produces a novel fusion protein, from which the protein of interest can be readily purified, in certain embodiments at substantially higher levels than can be achieved using only the sequence for the protein of interest alone, or using a linear configuration as described above.

Fusion polypeptides can be purified to high levels (greater than 80%, or greater than 90% pure, as visualized by SDS-PAGE) by undergoing further purification steps. Additional purification steps can be carried out and may be performed either before or after the IMAC column to yield highly purified protein. They present a major single band when analyzed by SDS PAGE under reducing conditions, and western blot analysis show less than 5% host cell protein contamination.

In one aspect, the present disclosure relates to a method of producing a fusion protein. The method comprises the steps of culturing a host cell transformed with an expression vector as described above, expression of that fusion protein in the respective host cell and separating the protein from the cell culture. The expression system is demonstrated to function with several distinct proteins as described herein, but it is expected it will function with a wide variety of distinct polypeptides with different structural and functional properties.

Compositions comprising fusion proteins, or proteins liberated from the fusion proteins of this disclosure are also provided. Such compositions include but are not necessarily limited to compositions that comprise a pharmaceutically acceptable excipient and thus are suitable for human and veterinary prophylactic and/or therapeutic approaches. In another embodiment, kits for producing fusion proteins according to this disclosure are provided. The kits can provide one or more expression vectors described herein, as well as printed instructions for using the vectors, and/or for recovering the overexpressed protein.

Although we have expressly designed the fusion protein to remain monomeric, it is plausible that it may domain swap in the cell, particularly if it is expressed at extremely high concentrations. If domain swapping occurs, the present invention will protect against proteolytic attack by blocking both termini of the target protein and allow for purification and recovery of the target protein.

The following Examples are intended to illustrate, but not limit the invention.

Example: GFP

Figure 4:
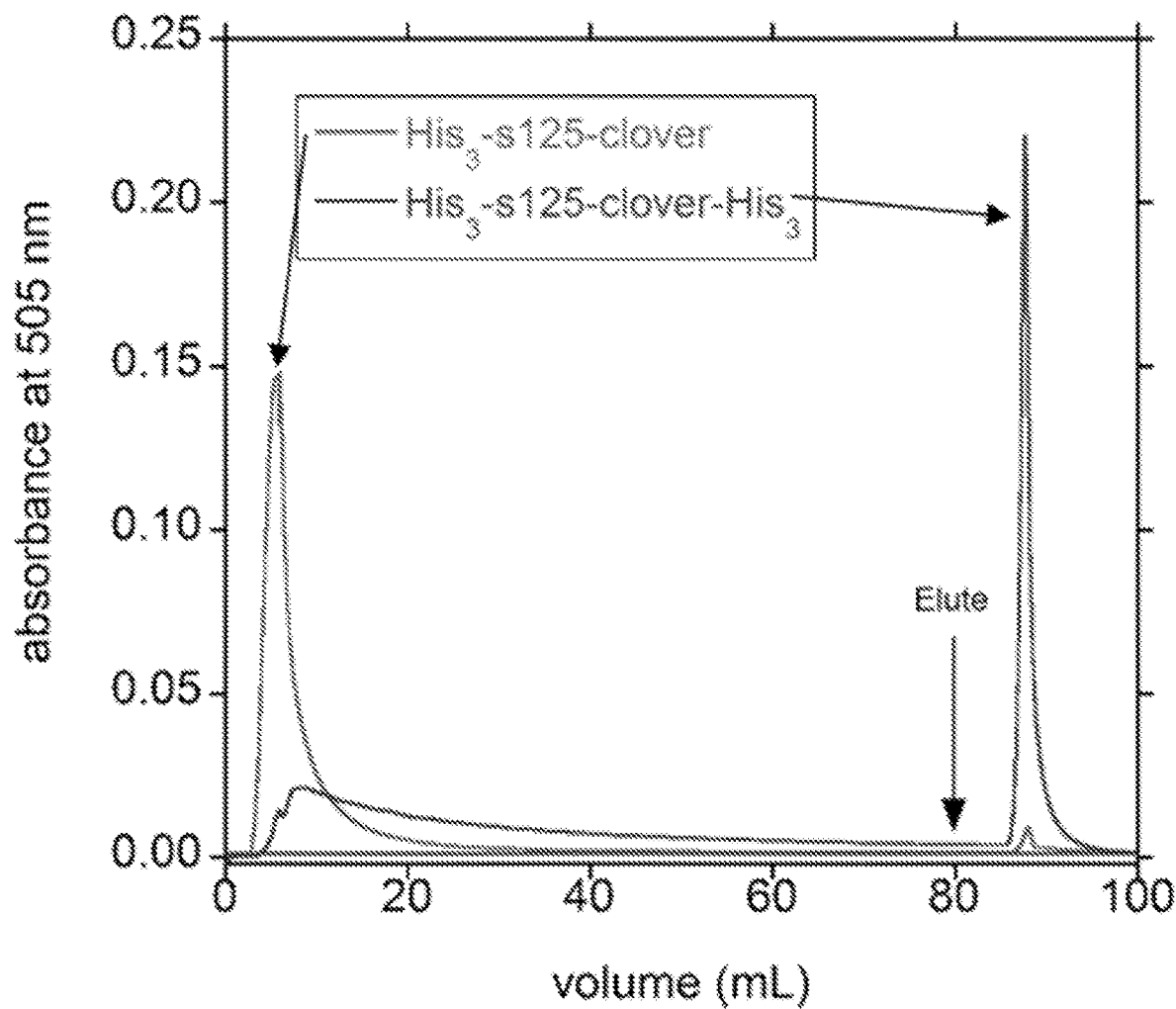
FIG. 4 provides comparison of purification chromatogram of s125-clover with one N-terminal His tag ($His_3$), with that of s125-clover with both N-($His_3$) and C-terminal ($His_3$) His tags. $His_3$-s125-clover does not bind to cobalt-NTA (nitrilotriacetic acid) resin in 20 mM imidazole while $His_3$-S125-clover-$His_3$ binds to the resin and is released at higher concentration of imidazole.

To demonstrate the effectiveness of the split-His tag design, we inserted a target protein (clover, a green fluorescent protein variant) into position 97 of RBP (FIG. 3A), and in a second construct, into position 125 of RBP to generate the construct (split-His)-(RBP 125-277)-(linker/cleavage site)-(clover)-(cleavage site/linker)-(RBP 1-124)-(split-His) (FIG. 3B). We designate these constructs as s97-clover and s125-clover, respectively (s97 means a target protein bracketed by linkers and cleavage sites was inserted into position 97 of the RBP). Permuting/splitting RBP at positions other than 97 is covered in this invention and is discussed in the next section. We chose to permute/split at position 125 because inspection of the X-ray structure of WT RBP suggested that the split-His tags would be oriented in a more parallel orientation than they would be when RBP is permuted at position 97. Thus, we reasoned that the metal binding affinity of the split-His tags in s125 constructs would be higher than in s97 constructs. We added $His_3$ tags to both termini of s125-clover ($His_3$-s125-clover-$His_3$). To mimic the products of proteolytic cleavage or incomplete transcription/translation, we created a second construct in which only a single $His_3$ tag was added to the N-terminus ($His_3$-s125- clover). We expressed the proteins in E. coli and loaded them on a $Co^{2+}$-agarose purification column. As expected, the single $His_3$ tag was too short to facilitate binding of $His_3$-s125-clover to the column; nearly all of the protein flowed through in the wash and only a tiny peak eluted in the 0.15 M imidazole elution step (FIG. 4). In marked contrast, most of the $HiS_3$-s125-clover-$HiS_3$ protein bound to the column, with a large, sharp peak coming off with the 0.15 M imidazole elution. FIG. 4 demonstrates that the full-length fusion protein, which contains both halves of the split-$His_3$ tag, can be efficiently separated from degraded and or incompletely transcribed/translated species that only contain a single $His_3$ tag.

Figure 5:
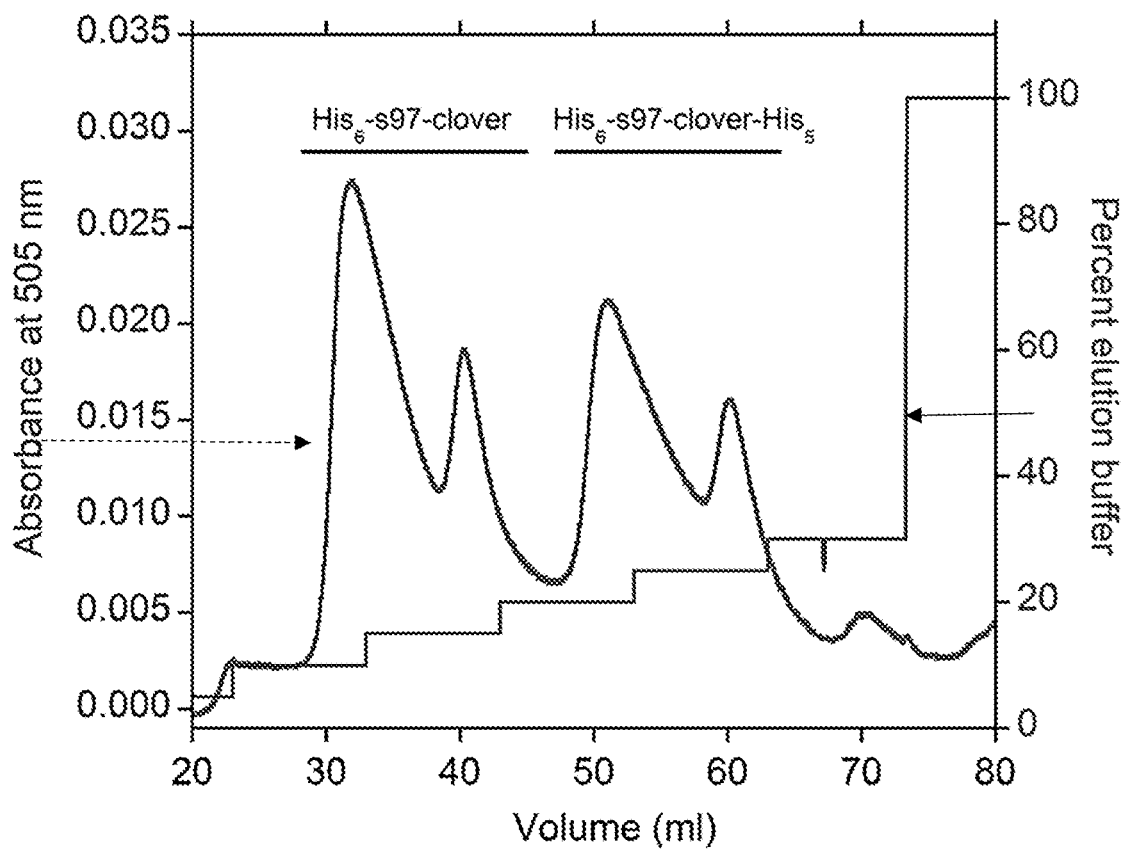
FIG. 5 provides comparison of purification chromatogram of s97-clover with one N-terminal His tag ($His_6$) with that of s97-clover with both N-($His_6$) and C-terminal (Hiss) His tags. Both proteins bind to nickel-NTA resin in 10 mM imidazole, but $His_6$-597-clover is released at lower concentration of imidazole than $His_6$-597-clover-$HiS_5$ protein.

As an additional demonstration of the ability of split-His tag to selectively purify full-length proteins, we performed a similar experiment with $His_6$-s97-clover-Hiss (and $His_6$-597-clover as the single-His tag control). To more closely replicate real-world purification, we pre-mixed the two proteins before loading them onto a $Ni^{2+}$ column. FIG. 5 shows that $His_6$-s97-clover elutes earlier in the imidazole step gradient compared to $His_6$-s97-clover-Hiss, again demonstrating that the split-His tag can resolve full-length from truncated products.

Example: Lect2 Protein Overexpression Via Split-RBP Vs. Linear RBP Vs. Tagless

Figure 6:
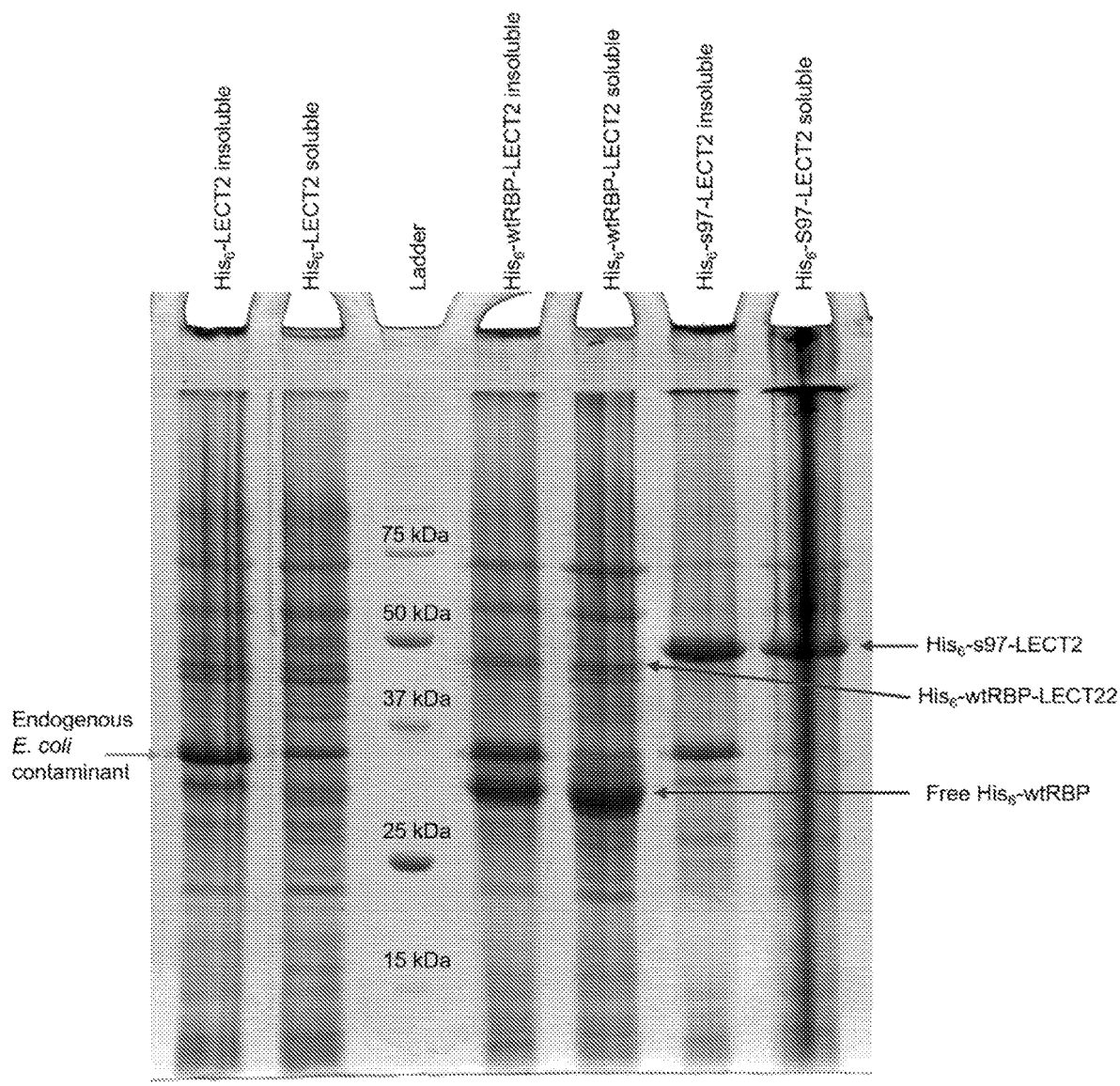
FIG. 6 provides a photographic representation of a SDS-polyacrylamide (SDS-PAGE) gel stained with Coomassie dye demonstrating that $His_6$-LECT2 (14 kDa) does not express to detectable levels. Similarly, $His_6$-wtRBP-LECT2 expresses poorly; the major species present is the truncated species $His_6$-wtRBP. By contrast, $His_6$-597-LECT2 L is expressed at high levels, with the full-length protein being the major species present.

Here we demonstrate that the split, circularly permuted RBP expression tag is superior to both the linear RBP and tagless systems for overexpressing the protein LECT2. LECT2 is the protein that causes the $4^{th}$ most common form of systemic amyloidosis in the United States. Lect2 has three disulfide bonds. When Lect2 was previously expressed in E. coli, it did not fold properly because the disulfide bonds became scrambled. Lect2 expressed as S97 fusion protein was not only soluble but also has all three disulfide bonds correctly formed according to Mass Spec. We made three LECT2 constructs. For the first we inserted LECT2 into position 97 of split-RBP (as shown in FIG. 3A) to create $His_6$-597-LECT2. For the second we fused wild-type, non-permuted RBP to the N-terminus of LECT2 to create $His_6$-wtRBP-LECT2. For the third we simply added a $His_6$-tag to the N-terminus of LECT2 to generate $His_6$-LECT2. We then expressed the proteins under identical conditions in E. coli, lysed the cells, and ran the insoluble and soluble fractions on an SDS-polyacrylamide gel. FIG. 6 shows that $His_6$-LECT2 (14 kDa) does not express to detectable levels. Similarly, $His_6$-wtRBP-LECT2 expresses poorly; the major species present is the truncated species $His_6$-wtRBP. By contrast, $His_6$-597-LECT2 is expressed at high levels, with the full-length protein being the major species present. Importantly, truncation products (e.g. the s97 fragments of 11 kDa and 20 kDa) are not detected. These results indicate that: (1) the s97 tag greatly enhances expression of LECT2, and (2) the closed, topologically circular topology created by the s97-LECT2 fusion seems to protect the full-length protein from degradation, compared to the linear wtRBP-LECT2 fusion.

Example: Expression of Human Double-Minute Protein 2 (MDM2)

Figure 7:
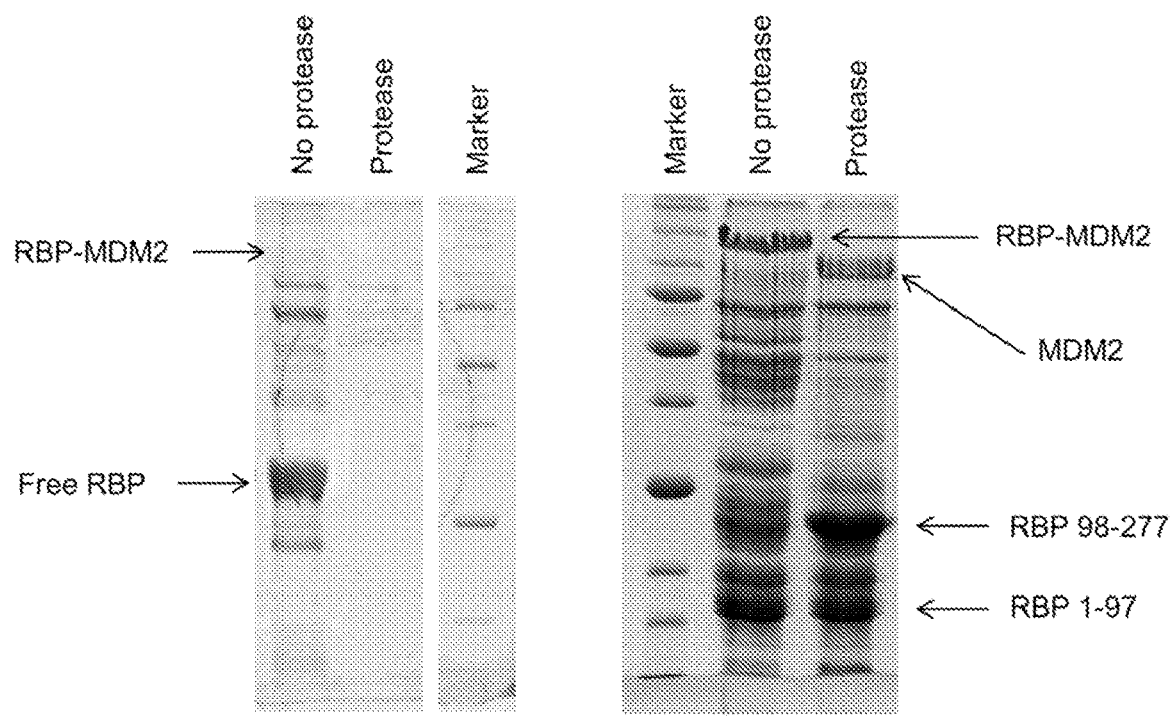
FIG. 7 provides a photographic representation of a SDS-PAGE gel stained with Coomassie dye demonstrating that $His_6$-wtRBP MDM2 does not express to detectable levels (left panel). By contrast, $His_6$-s97-MDM2 is expressed at high levels (right panel).

MDM2 is a high-value target for protein expression because it is the major negative regulator for the p53 tumor suppressor. Disrupting the MDM2-p53 interaction is a major target for developing anti-cancer drugs, but these efforts have been hindered by the inability to express full-length MDM2 in sufficient quantity. We directly compared MDM2 expression using the split, circularly permuted RBP system of the present invention versus a linear RBP embodiment. The MDM2 gene was appended to or inserted in the RBP gene as shown in FIG. 3A, with appropriate linkers (see FIG. 9b for gene and protein sequences). E. coli cultures were grown, induced, harvested, and lysed under identical conditions. FIG. 7 shows the eluents from the nickel column. Five times as many cells were lysed for the linear RBP data.

The linear RBP system prep (left) shows a faint, barely detectable band of full-length RBP-MDM2 eluting from the nickel column. By contrast, the free RBP band is very intense. The example of the current disclosure (right) indicates an intense band of full-length RBP-MDM2 (again, generated from ⅕ as many cells as the linear control) with less contamination with RBP fragments.

We digested the solutions with protease to release free MDM2. In the linear RBP system prep, we then passed the solution over nickel beads to remove the free RBP contaminant. No MDM2 band was observed in the gel. In contrast, for the permuted circular tag, we digested with protease but did not pass the solution over nickel beads. We observe nearly complete cleavage of full-length RBP-MDM2 to yield an intense band of free MDM2. Thus, the present disclosure provides a significant improvement in protein production/purification relevant to a control.

Example: Expression of p53

Figure 8:
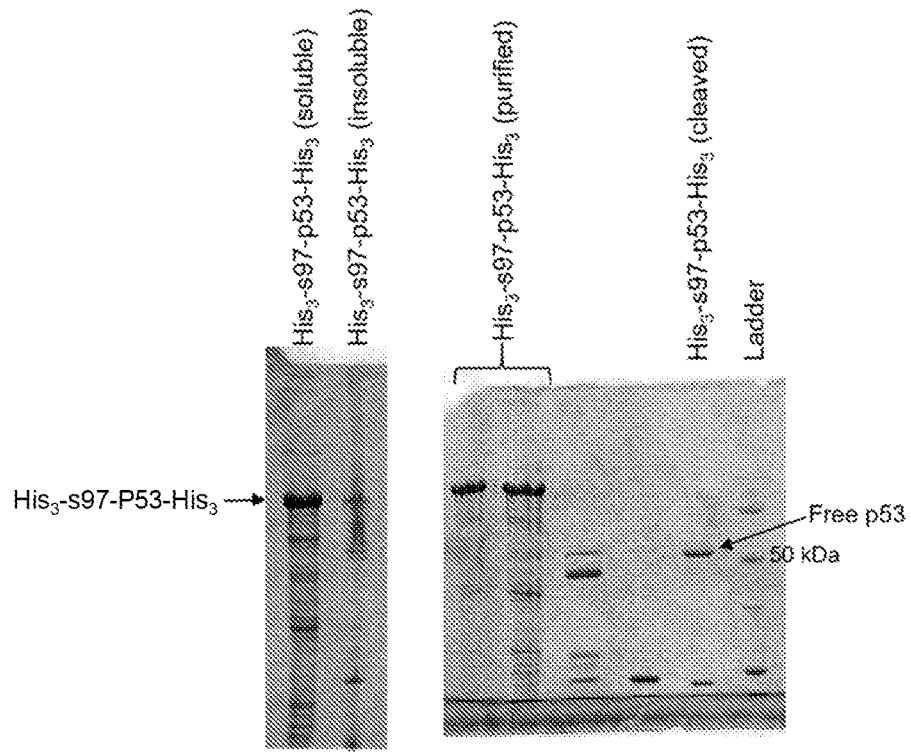
FIG. 8 provides a photographic representation of a SDS-PAGE gel stained with Coomassie dye demonstrating that $His_3$-597-P53-$His_3$ is expressed at high levels (left panel). The fusion protein is digested with HRV3C protease on Nickel-NTA resin and eluted with one other contaminant (right panel).

We inserted human p53 into position 97 of split, circularly permuted RBP (as shown in FIG. 3A) to create $His_3$-597-p53-$His_3$. FIG. 8 (left gel) indicates that full-length $His_3$-s97-p53-$His_3$ is overexpressed to a high level in E. coli lysates, with the majority of the protein found in the soluble fraction. P53 alone, without being fused to s97 or wtRBP, does not express to detectable levels (not shown). FIG. 8 (right gel) demonstrates that the split-His tag enables purification of the full-length protein to homogeneity, and that subsequent cleavage with prescission protease yields the correct, native p53 protein. This protein was determined to be fully functional by DNA binding assays (not shown).

The following is a non-limiting protocol by which an embodiment of this disclosure can be performed.

One Column Purification of the Target Protein
1. Transform BL21(DE3) cells (or one of its derivatives) with an appropriate plasmid (e.g. pET41 sRBP-mdm2) as described herein.
2. Inoculate one colony in 1 liter of LB and grow at 30° C. until $OD_{600}$~0.6.
3. Induce the protein expression with Isopropyl β-D-galactopyranoside (0.1 to 0.4 mM) at 18° C. and further incubate the media for 16 to 19 hours with vigorous shaking at 18° C.
4. Spin down cells and freeze on dry ice.
5. Lyse cells in 10 mM Tris, pH 8.0, 0.3 to 0.5 M NaCl, 10 mM Imidazole (Buffer A).
6. Remove insoluble material by centrifugation and load the soluble fraction onto ~15 ml of Ni-NTA (or Co-NTA) resin which is pre-equilibrated in Buffer A.
7. Wash the resin with Buffer A until the absorbance at 260 and 280 reaches the buffer level.
8. Add HisTag-RBP-HRV3C Protease (1 to 2% (w/w) of the target protein) to the resin and gently mix at 4° C. overnight.
9. Collect the flow through and further wash the resin with Buffer A till OD280~0.

If the target protein has free thiols, β-mercaptoethanol or a reagent with a similar function should be present.

In some cases, it is preferable to elute target protein fused to split RBP from the resin and then mix HRV3C protease (or any other protease) to the fusion protein.

While the disclosure has been particularly shown and described with reference to specific embodiments, it should be understood by those having skill in the art that various changes in form and detail may be made therein without departing from the spirit and scope of the present disclosure as disclosed herein.

What is claimed is:

1. An expression vector encoding a polypeptide, the polypeptide comprising sequentially in an N to C terminal direction:
   a) optionally at the N-terminus of the polypeptide a first Histidine sequence that can function as a component of a functional Histidine tag with a second Histidine sequence located at the C-terminus of the polypeptide;
   b) a first segment of a Ribose Binding Protein (RBP);
   c) a first linker sequence;
   d) optionally a first protease cleavage site;
   e) a second linker sequence;
   f) a second segment of the RBP,
   wherein the second segment is located N-terminal to the first segment relative to an intact wild type amino acid sequence of an RBP comprising the sequence of SEQ ID NO:1; and
   g) optionally at the C-terminus of the polypeptide a second Histidine sequence that can function with the first Histidine sequence in the functional Histidine tag, wherein optionally the functional His tag if present has improved metal binding relative to either of the first or second His tags alone,
   wherein the amino acid sequence of the first segment and the amino acid sequence of the second segment together comprise an amino acid sequence that has at least 90% identity with a segment of SEQ ID NO:1 that is at least 251 amino acids in length, and wherein the amino acid sequences of the first and second segments do not overlap with each other,
   and wherein the first linker and the second linker, and the first protease cleavage site if present, and the second protease cleavage site if present, together comprise at least thirty amino acids.

2. The expression vector of claim 1, wherein the segment of SEQ ID NO:1 that is at least 251 amino acids in length is amino acids 4-254 of SEQ NO:1.

3. The expression vector of claim 1, wherein the first segment comprises a contiguous amino acid sequence that has at least 90% identity with a segment of SEQ ID NO:1 that is amino acids 34-254 of SEQ ID NO:1, 60-254 of SEQ ID NO:1, 70-254 of SEQ ID NO:1, 85-254 of SEQ ID NO:1, 97-254 of SEQ ID NO:1, 125-254 of SEQ ID NO:1, 136-254 of SEQ ID NO:1, 186-254 of SEQ ID NO:1, or 210-254 of SEQ ID NO:1, thereby having the first amino acid of the first segment as amino acid 34, 60, 70, 85, 97, 125, 136, 186 or 210 of SEQ ID NO:1, and wherein the first segment is optionally extended by any number of amino acids up to amino acid number 277 of SEQ ID NO:1.

4. The expression vector of claim 1, wherein the second segment comprises a contiguous amino acid sequence that has at least 90% identity with a segment of SEQ ID NO:1 that begins with amino acid number 1, 2, 3, or 4 of SEQ ID NO:1 and ends with amino acid number 33, 59, 69, 84, 96, 124, 135, 185, or 209 of SEQ ID NO:1.

5. The expression vector of claim 1, wherein the second segment comprises a contiguous amino acid sequence of SEQ ID NO:1 that begins with amino acid number 1, 2, 3, or 4 of SEQ ID NO:1 and ends with amino acid number 33, 59, 69, 84, 96, 124, 135, 185, or 209 of SEQ ID NO:1.

6. The expression vector of claim 5, wherein the second segment ends at amino acid 96 or amino acid 124 of SEQ ID NO:1.

7. The expression vector of claim 1, wherein: i) the at least one restriction endonuclease digestion site is present in a multiple cloning site within the expression vector; and/or ii) the expression vector further encodes at least one protease cleavage site located between the at least one restriction endonuclease digestion site and the first or the second linker sequence; and/or iii) the first and/or the second linker is at least 15 amino acids in length.

8. The expression vector of claim 7, wherein the at least one restriction endonuclease digestion site is present in the multiple cloning site and the first and/or the second linker is at least 15 amino acids in length.

9. A method comprising allowing expression of the expression vector of claim 7 such that a fusion protein is expressed, with the proviso that a polynucleotide sequence encoding a target protein is inserted into the multiple cloning site, and wherein the expressed fusion protein comprises the first and second Histidine sequences, the first and second segments of the Ribose Binding Protein, the first and second linker sequences, and the at least one protease cleavage site if the protease cleavage site is encoded by the expression vector.

10. The method of claim 9, wherein first and the second linker are at least 15 amino acids in length.

11. The method of claim 10, further comprising exposing the fusion protein to a metal such that the first and second Histidine sequences form a functional Histidine tag that forms a non-covalent association with the metal.

12. The method of claim 11, further comprising separating the fusion protein from the metal.

13. The method of claim 10, wherein the fusion protein comprises the at least one protease cleavage site and optionally comprises a second protease cleavage site such that the first and second protease cleavage sites flank the target protein, the method further comprising cleaving the fusion protein at the first or the first and the second protease cleavage sites, and optionally purifying a protein cleavage product that comprises the target protein.

14. The method of claim 9, wherein the expression of the vector is in prokaryotic cells.

15. A population of cells comprising an expression vector of claim 7.

16. The population of cells of claim 15, wherein the cells are prokaryotic cells.

17. A population of prokaryotic cells comprising an expression vector of claim 8.

18. A fusion protein produced by the method of claim 9.

19. A kit comprising an expression vector of claim 7.

20. The kit of claim 19, further comprising printed instructions for using the expression vector to produce the fusion protein.

21. An expression vector encoding a polypeptide, the polypeptide comprising sequentially in an N to C terminal direction:
   a) a first segment of a Ribose Binding Protein (RBP);
   b) a first linker sequence;
   c) optionally a first protease cleavage site;
   d) optionally a second protease cleavage site;
   e) a second linker sequence;
   f) a second segment of the RBP;
   wherein the expression vector optionally comprises a first Histidine sequence located at the N-terminus of the polypeptide and/or C-terminus of the polypeptide;
   wherein the amino acid sequence of the first segment and the amino acid sequence of the second segment together comprise an amino acid sequence that has at least 90% identity with a segment of SEQ ID NO:1 that is at least 251 amino acids in length, and wherein the amino acid sequences of the first and second segments do not overlap with each other; and
   wherein the first linker and the second linker, and the first protease cleavage site if present, and the second protease cleavage site if present, together comprise at least thirty amino acids.

22. The expression vector of claim 21, wherein the first segment comprises a contiguous amino acid sequence that has at least 90% identity with a segment of SEQ ID NO:1 that is amino acids 34-254 of SEQ ID NO:1, 60-254 of SEQ ID NO:1, 70-254 of SEQ ID NO:1, 85-254 of SEQ ID NO:1, 97-254 of SEQ ID NO:1, 125-254 of SEQ ID NO:1, 136-254 of SEQ ID NO:1, 186-254 of SEQ ID NO:1, or 210-254 of SEQ ID NO:1, thereby having the first amino acid of the first segment as amino acid 34, 60, 70, 85, 97, 125, 136, 186 or 210 of SEQ ID NO:1, and wherein the first segment is optionally extended by any number of amino acids up to amino acid number 277 of SEQ ID NO:1.

23. The expression vector of claim 21, wherein the first segment ends at amino acid 277 of SEQ ID NO:1.

24. The expression vector of claim 21, wherein: i) the expression vector comprises at least one restriction endonuclease digestion site in a multiple cloning site; and/or ii) the expression vector further encodes at least one protease cleavage site located between the at least one restriction endonuclease digestion site and the first or the second linker sequence; and/or iii) the first and/or the second linker is at least 20 amino acids in length, and wherein the second segment comprises a contiguous amino acid sequence that has at least 90% identity with a segment of SEQ ID NO:1 that begins with amino acid number 1, 2, 3, or 4 of SEQ ID NO:1 and ends with amino acid number 33, 59, 69, 84, 96, 124, 135, 185, or 209 of SEQ ID NO:1.

25. A method comprising allowing expression of the expression vector of claim 21 such that a fusion protein is expressed, with the proviso that a polynucleotide sequence encoding a target protein is inserted into the multiple cloning site, and wherein the expressed fusion protein comprises the first and second Histidine sequences, the first and second segments of the RBP, the first and second linker sequences, and the at least one protease cleavage site if the protease cleavage site is encoded by the expression vector.

26. A cell comprising an expression vector of claim 21.

27. A fusion protein produced by the method of claim 25.

28. A kit comprising an expression vector of claim 22.

* * * * *